US008080789B2

(12) United States Patent
Nasu et al.

(10) Patent No.: US 8,080,789 B2
(45) Date of Patent: Dec. 20, 2011

(54) SAMPLE DIMENSION MEASURING METHOD AND SCANNING ELECTRON MICROSCOPE

(75) Inventors: Osamu Nasu, Hitachinaka (JP); Tadashi Otaka, Hitachinaka (JP); Hiroki Kawada, Tsuchiura (JP); Ritsuo Fukaya, Hitachinaka (JP); Makoto Ezumi, Mito (JP)

(73) Assignee: Hitachi, Ltd., Tokyo (JP)

( * ) Notice: Subject to any disclaimer, the term of this patent is extended or adjusted under 35 U.S.C. 154(b) by 176 days.

(21) Appl. No.: 12/560,091

(22) Filed: Sep. 15, 2009

(65) Prior Publication Data

US 2010/0038535 A1 Feb. 18, 2010

Related U.S. Application Data

(62) Division of application No. 10/450,852, filed as application No. PCT/JP02/02983 on Mar. 27, 2002, now Pat. No. 7,659,508.

(30) Foreign Application Priority Data

Aug. 29, 2001 (JP) .................... 2001-259126

(51) Int. Cl.
*H01J 37/28* (2006.01)
*G01N 23/225* (2006.01)
(52) U.S. Cl. ......................... 250/310; 250/307
(58) Field of Classification Search .................. 250/310, 250/307
See application file for complete search history.

(56) References Cited

U.S. PATENT DOCUMENTS

| 4,189,641 | A | 2/1980 | Katagiri et al. |
| 5,276,325 | A | 1/1994 | Todokoro et al. |
| 5,912,462 | A | 6/1999 | Takami et al. |
| 6,528,229 | B2 | 3/2003 | Sato |
| 6,815,677 | B2 | 11/2004 | Nagai et al. |
| 7,218,126 | B2 * | 5/2007 | Cheng et al. ............... 250/310 |
| 7,285,777 | B2 * | 10/2007 | Kawada et al. ............ 250/307 |
| 7,659,508 | B2 * | 2/2010 | Nasu et al. ................ 250/310 |
| 7,910,886 | B2 * | 3/2011 | Kawada et al. ............ 250/310 |

FOREIGN PATENT DOCUMENTS

| JP | 53-030865 | 3/1978 |
| JP | 53-30865 | 3/1978 |
| JP | 57-27548 | 2/1982 |

(Continued)

OTHER PUBLICATIONS

"Scanning Electron Microscoopy" by Michael T. Postek, Jr. and Ladd Research Industries, Inc., pp. 30-33 (1980).

*Primary Examiner* — Jack Berman
(74) *Attorney, Agent, or Firm* — Dickstein Shapiro LLP

(57) ABSTRACT

The present invention suppresses decreases in the volumes of the patterns which have been formed on the surfaces of semiconductor samples or of the like, or performs accurate length measurements, irrespective of such decreases. In an electrically charged particle ray apparatus by which the line widths and other length data of the patterns formed on samples are to be measured by scanning the surface of each sample with electrically charged particle rays and detecting the secondary electrons released from the sample, the scanning line interval of said electrically charged particle rays is set so as not to exceed the irradiation density dictated by the physical characteristics of the sample. Or measured length data is calculated from prestored approximation functions.

4 Claims, 22 Drawing Sheets

FOREIGN PATENT DOCUMENTS

| | | |
|---|---|---|
| JP | 59-179530 A | 10/1984 |
| JP | 59-201351 A | 11/1984 |
| JP | 59-214151 | 12/1984 |
| JP | 61-148312 A | 7/1986 |
| JP | 61-265517 A | 11/1986 |
| JP | 62-192609 A | 8/1987 |
| JP | 63-76252 A | 4/1988 |
| JP | 02-159508 | 6/1990 |
| JP | 05-074399 | 3/1993 |
| JP | 07-063542 | 3/1995 |
| JP | 09-050778 | 2/1997 |
| JP | 09-166428 | 6/1997 |
| JP | 9-166428 | 6/1997 |
| JP | 10-50245 A | 2/1998 |
| JP | 11-237230 | 8/1999 |
| JP | 2001-147112 | 5/2001 |

* cited by examiner

IMAGE DISPLAYED ON
SAMPLE IMAGE DISPLAY UNIT

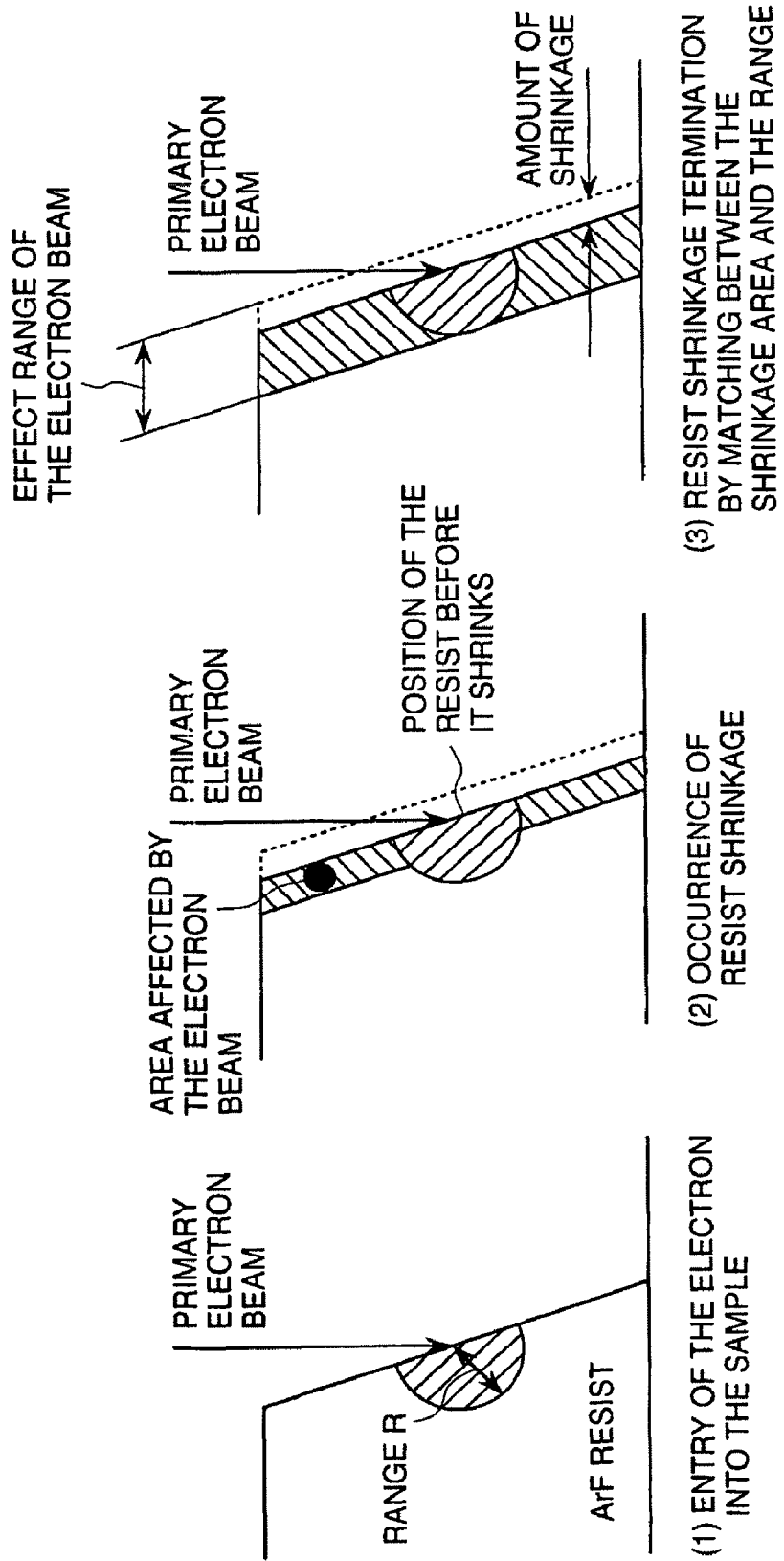

FIG. 13C
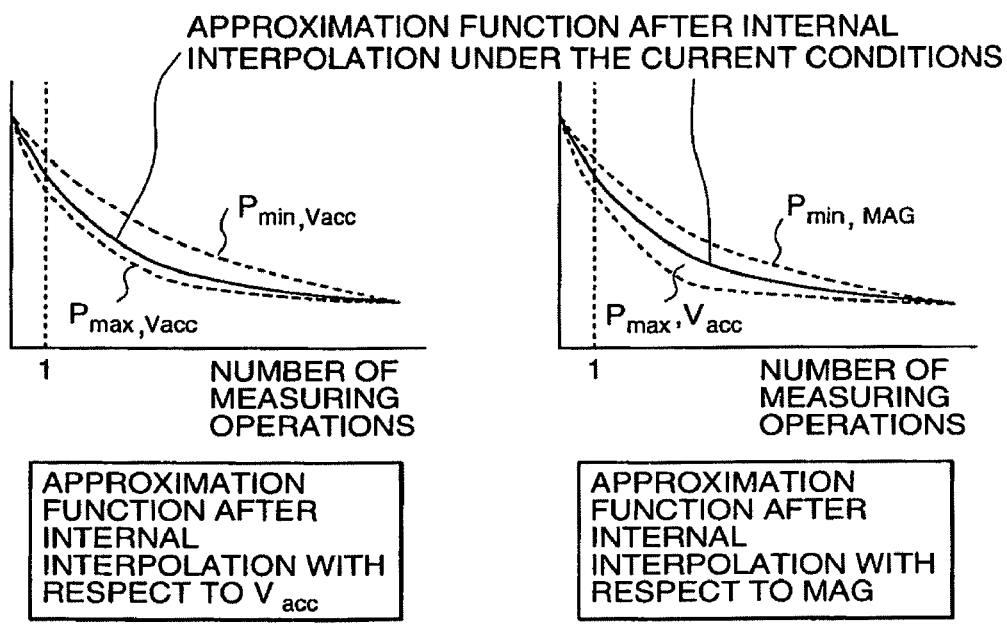
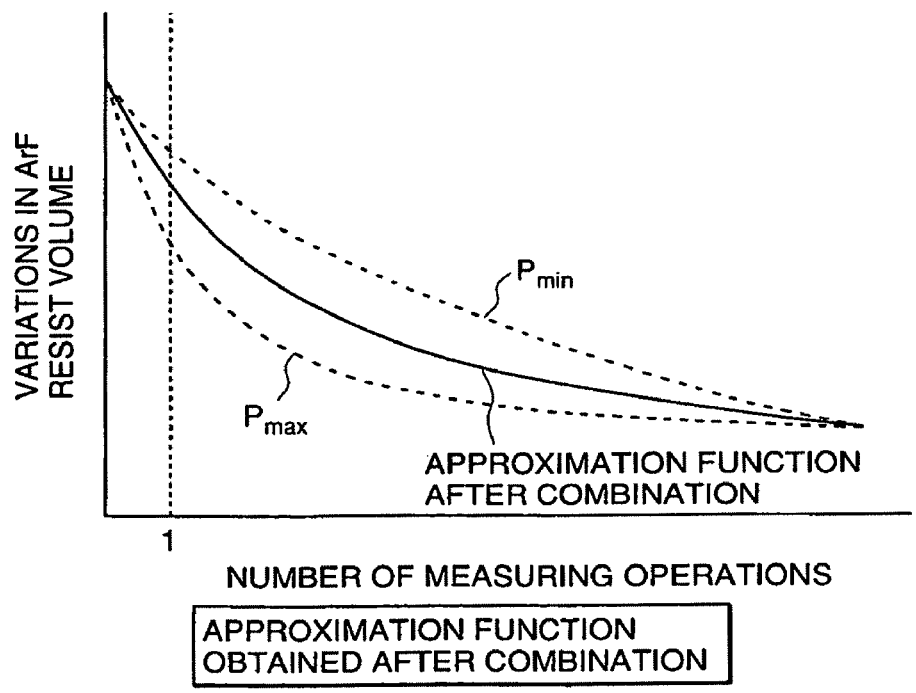

SAMPLE DIMENSION MEASURING METHOD AND SCANNING ELECTRON MICROSCOPE

The present application is a divisional of U.S. application Ser. No. 10/450,852, Jun. 18, 2003 now U.S. Pat. No. 7,659,508 which was the National stage of International Application No. PCT/JP02/02983, Mar. 27, 2002 the entire disclosure of which is incorporated herein by reference.

BACKGROUND OF THE INVENTION

The present invention relates to a method of measuring the dimensions of microstructured patterns by use of a scanning electron microscope, and to the scanning electron microscope to be used for the above measurement; the invention relates more particularly to a method in which the dimensions of the samples varying in shape are to be measured by radiating electron beams, and to the scanning electron microscope to be used for the above measurement.

During the manufacture and inspection of semiconductor devices, thin-film magnetic heads, and other functional element products by use of microstructured surface processing, scanning electron microscopes are commonly used to measure the widths of processed patterns (hereinafter, this measurement process is referred to as length measurement) and to visually inspect the patterns.

The conventional scanning type of electron microscope is an apparatus intended to form images of samples, wherein the electron beam that has been emitted from an electron source and dimensionally restricted by a convergent lens/object lens combination which utilizes the mutual action between a magnetic field or an electric field and the electron beam is applied to the sample for its one-dimensional or two-dimensional scanning by use of a deflector, then the secondary signals (secondary electron, reflected electron, and electromagnetic wave) that have been generated from the sample by the irradiation of the electron beam are detected using a detector which utilizes a photo-electric effect or the like, and the detected signals are converted and processed into visible signals such as luminance signals synchronized with electron beam scanning of the sample (hereinafter, these signals are referred to as "image signals").

For the conventional scanning type of electron microscope, efforts are exerted so that the image corresponding to the shape of the sample to be observed and measured in length can be obtained with high accuracy. That is to say, when the surface of a sample is observed, conversion/processing into image signals takes place in a plane area accurately analogous to the corresponding scan area (hereinafter, the plane area is referred to as the image area), and the image signals from the various points in the scan area are also arranged at positions accurately analogous to those of the scan area. This arrangement can usually be implemented by:

1) Making both the scan area and the image area rectangular and constituting one side of each rectangle as length with the same number of scanning lines, and 2) Matching the scan area and the image area in terms of the ratio between the scanning line length and the scanning line-to-line distance.

Thus, the distance between any two points on the sample surface always has a constant ratio with respect to the distance between the corresponding two points on the sample image. This ratio is the magnification of the scanning electron microscope. Such an art has already been commonly realized as the basic technology for constructing a scanning electron microscope, and this art is described in, for example, on pages 2 onward of "SCANNING ELECTRON MICROSCOPY", a writing by L. Reimer, a German scientist.

In addition, the distance between any two points on the sample surface can be easily calculated from the thus-obtained sample image. This calculation is generally called "length measurement", and a scanning electron microscope having the relevant calculating function is called the "length-measuring electron microscope."

Japanese Application Patent Laid-Open Publication No. 2001-147112, on the other hand, describes an example in which the scan area on the sample surface and the sample image are not analogous. In this example, in order to dimensionally measure the patterns of a sample that absolutely require reduction in magnification because each pattern is spaced in spite of consisting of very small elements, an image of the sample is prolonged in a vertical direction with respect to the straight line connecting any two points on the sample. Thus, a secondary electron image is formed for improved dimensional measuring accuracy.

SUMMARY OF THE INVENTION

For the conventional scanning electron microscope, an electron beam with an attainable energy level of at least several hundreds of electron volts is, of course, irradiated onto the surface of the sample to be observed.

In recent years, the microstructured processing levels of semiconductor surfaces have been further enhanced and an argon fluoride (ArF) photoresist, which is one type of photoresist reacting to, for example, argon fluoride (ArF) eximer laser light, has come to be used.

It is believed that since the ArF laser beam has a short wavelength of 160 nm, the ArF photoresist is suitable for exposure of further microstructured circuit patterns. Through recent closer studies, however, it has come to be known that since the ArF laser beam is very brittle against electron beam irradiation, when a formed pattern is observed or measured using a scanning electron microscope, the acrylic resin and other components of the base material will suffer condensation reaction due to the convergent electron beam scan and the resulting decrease in volume (hereinafter, this event is called "shrinkage") will change the shape of the circuit pattern.

For a semiconductor device, the shape and dimensions of its circuit pattern must be strictly managed to achieve the design performance of the device, and for this reason, a length-measuring electron microscope capable of measuring micro-dimensions is used during the inspection process. However, there is the problem that since, during the observing and measuring processes, electron beam irradiation for length measurement changes the shape of the pattern, the desired circuit pattern design data cannot be obtained and this causes the deterioration of the device in characteristics and/or its destruction.

There is also the problem that since line width changes, even when the same dimension is measured, measured data disperses with each measuring operation and measuring accuracy does not improve. At present, there exists no apparatus that replaces the length-measuring type of electron microscope in that micro-dimensions can be measured with the desired accuracy, and the shrinkage of patterns is a major bottleneck in the semiconductor device manufacture that uses the ArF photoresist. For the conventional type of scanning electron microscope, therefore, no attention is paid to the shrinkage of samples during electron beam irradiation and there has been a problem with the accuracy of measured pattern dimensional data. Referring again to Japanese Application Patent Laid-Open Publication No. 2001-147112 mentioned earlier in this Specification, one can see that although attention is paid to the accuracy of dimension measurement between any two points distanced on the sample, no attention is paid to the shrinkage of the sample during the irradiation of the electron beam.

The first object of the present invention is to suppress the shrinkage of patterns, which are likely to suffer shrinkage due to electron beam irradiation during measurement, and thus to enable accurate dimension measurement of these patterns.

The second object of the present invention is to enable accurate measurement of pattern dimensions, irrespective of whether their shrinkage occurs.

In order to achieve the above-mentioned first object, by use of a scanning electron microscope equipped with an electron source, with a scanning means by which the surface of the sample placed on a sample mounting stage is to be scanned two-dimensionally using an electron beam emitted from the electron source, with a detection means for detecting the electrically charged particles or electromagnetic waves released from the sample by the irradiation of the electron beam, and with an arithmetic unit which arithmetically measures the surface dimensions of the sample from the electrically charged particles or electromagnetic waves detected by the above-mentioned detection means, the present invention controls the scanning line interval within the scan area of the electron beam so that the irradiation density of the electron beam does not exceed the required value determined by the physical characteristics of the sample.

Also, in order to achieve the above-mentioned second object, in the method where a sample is to be scanned using an electron beam and the dimensions of the pattern formed on the sample are to be measured using the information obtained from the detection of an electron emitted from the scanned section, the present invention calculates beforehand the function that denote changes in the decreases of the above pattern dimension, associated with the irradiation of the electron beam to the sample, and calculates the original dimensions of the pattern from the corresponding function and from the length data obtained by the scanning of the sample with the electron beam.

Further details of the composition and effectiveness of the prevent invention are described in the section pertaining to the preferred embodiments of the invention.

BRIEF DESCRIPTION OF THE DRAWINGS

FIG. 4 is a view explaining the outline of shrinkage due to the mutual action between a photoresist and an electron beam.

DETAILED DESCRIPTION OF THE PREFERRED EMBODIMENTS

Figure 1:
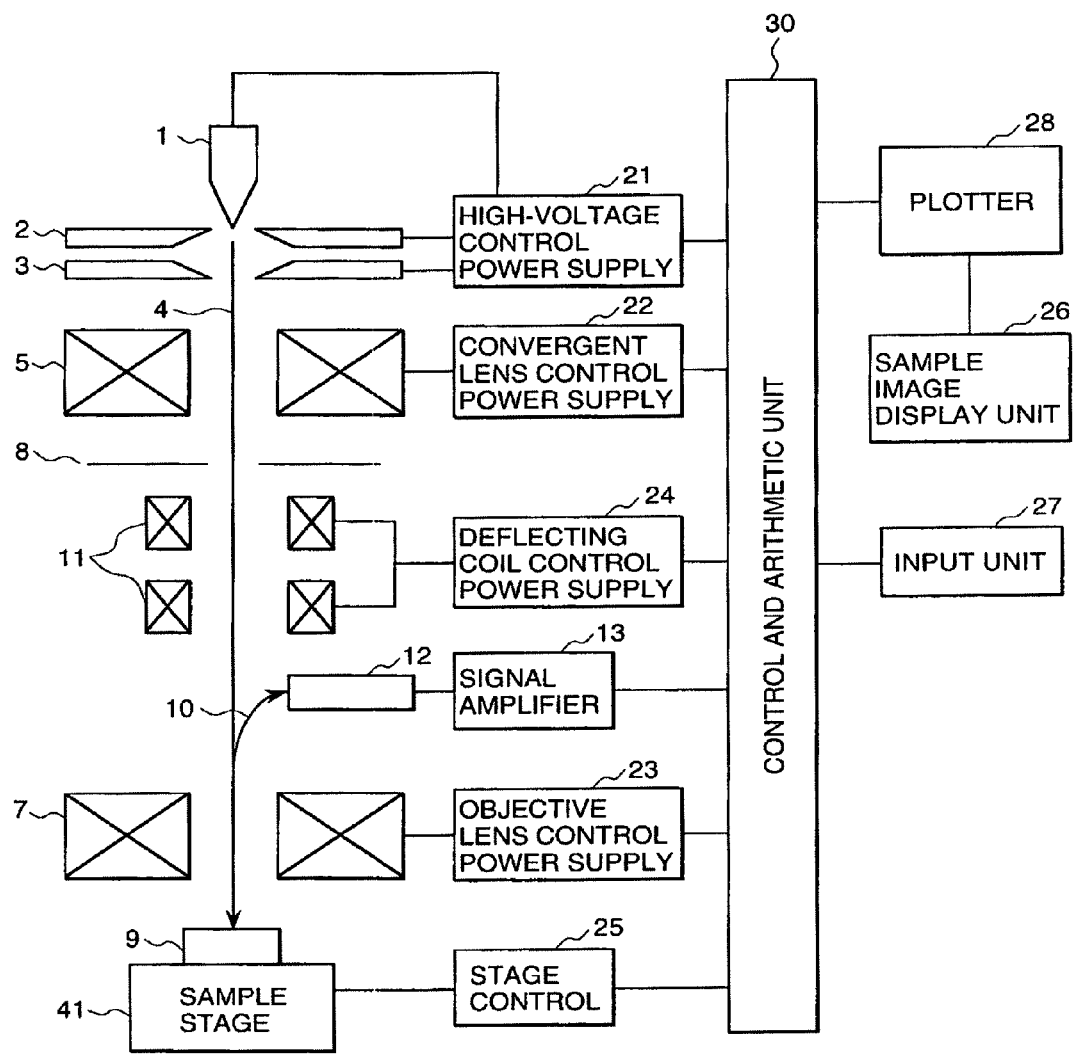
FIG. 1 is a block diagram of the scanning electron microscope shown as an embodiment of the present invention.

FIG. 1 is a block diagram of the scanning electron microscope shown as a first embodiment of the present invention. A voltage is applied between a cathode 1 and a first anode 2 by a high-voltage control power supply 21 controlled by a control and arithmetic unit 30 (control processor), and the required emission current is induced from the cathode 1. Since an acceleration voltage is applied between cathode 1 and a second anode 2 by the high-voltage control power supply 21 controlled by the control and arithmetic unit 30, a primary electron beam 4 that has been emitted from cathode 1 is accelerated and then moves into the lenses arranged at the succeeding stage. The primary electron beam 4 is converged by a convergent lens 5 controlled by a focusing lens control power supply 22, and an unnecessary area is removed from primary electron beam 4 by a diaphragm plate 8.

After this, primary electron beam 4 is further converged as a micro-spot on a sample 9 through an objective lens 7 controlled by an objective lens control power supply 23, and the surface of the sample is scanned two-dimensionally by a deflecting coil 11. The scanning signal from the deflecting coil 11 is controlled according to the particular observing magnification by a deflecting coil control power supply 24. Also, the sample 9 is fixed to the surface of a two-dimensionally movable sample stage 41. The movement of the sample stage 41 is controlled by a stage control portion 25.

A secondary electron 10 that has been generated from the sample 9 by the irradiation of the primary electron beam 4 is detected by a secondary electron detector 12. A plotter 28 converts detected secondary signals into visible signals and controls these signals so that they are arranged as appropriate on another plane. Hereby, the image corresponding to the surface shape of the sample is displayed as an image thereof on a sample image display unit 26.

An input unit 27, which functions as the interface between the operator and the control and arithmetic unit 30, and the operator controls each of the above-mentioned units via the input unit 27 and specifies measuring points and dimension measurement. A memory device not shown in the figure is provided in the control and arithmetic unit 30 so as to enable storage of measured length data.

After being amplified by a signal amplifier 13, the signals that have been detected by secondary electron detector 12 are stored into the internal image memory of the plotter 28. Although the apparatus according to this embodiment of the invention has a secondary electron detector 12, the configuration of the apparatus is not limited hereby; either a reflected electron detector for detecting reflected electrons or a detector for detecting light, electromagnetic waves, or X-rays, can be provided instead of or together with the primary electron detector.

The address signals corresponding to the memory locations within the image memory are created in control and arithmetic unit 30 or in a separately installed computer, and after undergoing analog conversion, the signals are supplied to deflecting coil 11. The address signals in the X-axial direction are digital addresses whose values cyclically change in order from 0 to 512 in the case that the image memory format is 512 pixels by 512 pixels, and the address signals in the Y-axial direction are digital addresses whose values cyclically change in order from 0 to 512 by being incremented by +1 when all values from 0 to 512 are reached as the value of each address signal in the X-axial direction. These signals are converted into analog signals.

Since linkage is established between the addresses within the image memory and the addresses of the deflection signals for electron beam scanning, the original secondary image of the electron beam in the deflecting area by the scanning coil is recorded in the image memory. The signals within the image memory can be sequentially read out in chronological order through a readout address creating circuit synchronized with a readout clock. The appropriate signals that have been read out according to address are converted into analog form and become the brightness modulation signals of the sample image display unit 28.

The image memory has a function that stores images (image data) in overlapped (combined) form for improved S/N ratio. For example, the images that have been obtained during eight two-dimensional scans are stored in overlapped form to form one complete image. In other words, the images that have been formed during one or more X-Y scans are combined to form the final image. The total number of frame images for creating one complete image can be arbitrarily set, and the appropriate value is usually set in consideration of conditions such as secondary electron generating efficiency. The desired final image can likewise be formed by overlapping a plurality of frame images on a plurality of existing frame images. Also, input of information to the image memory can be interrupted by blanking the primary electron beam when storage of the desired number of images is completed or hereafter.

In addition, it is possible to provide a sequence in which, after the total number of frame images has been set to eight, when the ninth frame image is acquired, the first frame image will be deleted and eight frame images left as a result, or to provide weighted additive averaging in which, when the ninth frame image is acquired, the total number of images stored within the image memory is multiplied by a factor of ⅞ and then the ninth frame image is added to the results.

The apparatus according to this embodiment of the invention also has a function that forms a line profile, subject to the detected primary electron, the reflected electron, or the like. The formation of the line profile is based on either the quantity of electrons detected during one-dimensional or two-dimensional scanning with the primary electron beam, or luminance information relating to the image of the sample, and the thus-obtained line profile is used for purposes such as measuring the dimensions of the pattern formed on a semiconductor wafer.

During the measurement of a pattern dimension, two vertical or horizontal cursor lines are displayed together with the sample image on the sample image display unit 26, then the two cursors are placed at two edges of the pattern via input unit 27, and the control and arithmetic unit 30 calculates the dimensions of the pattern from the information consisting of the sample image magnification and the distance between the two cursors.

Although the description of FIG. 1 assumes that the control processor operates integrally with the scanning electron microscope or by analogy therewith, the operation of the control processor is, of course, not limited by the description and such processing as described below can also be provided using a control processor provided independently of the scanning electron microscope. In that case, it is necessary to provide two types of elements. One is a transmission medium for transmitting to the control processor the signals detected by secondary electron detector 12 or for transmitting signals from the control processor to the lenses, deflector, and other components of the scanning electron microscope, and the other is input/output terminals for input and output of the signals transmitted via the above transmission medium. Or a program that is to undertake processing described below can be registered in a memory medium beforehand and then executed using a control processor provided with an image memory and capable of supplying the necessary signals to the scanning electron microscope.

In addition, the apparatus according to this embodiment of the invention has a function by which, for example, the section to be measured, the optical conditions of the scanning electron microscope, and other conditions for observing a plurality of points on a semiconductor are stored as a recipe beforehand and measurements and observations are conducted in accordance with the contents of the recipe.

Or a program that is to undertake processing described below can be registered in a memory medium beforehand and then executed using a control processor provided with an image memory and capable of supplying the necessary signals to the scanning electron microscope. That is to say, the embodiments of the present invention that are described below are such that both embodiments are also established as the invention of the program which can be adopted for an electrically charged particle ray apparatus such as a scanning electron microscope equipped with an image processor.

Embodiment 1

The shrinkage of the ArF photoresist pattern is likely to be caused by the chemical reaction due to the convergent electron beam entering the photoresist. The inventors have therefore performed experiments in order to empirically derive the relationship between the acceleration voltage $V_{acc}$ to the pattern of the convergent electron beam, electron beam current density $I_{pd}$, and the amount of shrinkage. As a result, 2S (the amount of shrinkage at both edges of a linear pattern in the case that the amount of shrinkage at one edge is taken as S) has obeyed empirical formula (1).

$$2S = K1 \cdot V_{acc}{}^{K2} \cdot \{1 - \exp(-(I_{pd}{}^{0.5} \cdot n/K3))\} \quad (1)$$

where 2S: the amount of shrinkage at both edges, $V_{acc}$: the acceleration voltage (V), K1, K2, K3: parameters determined by the photoresist, and n: the number of measuring operations. It can therefore be seen that to suppress the shrinkage of the ArF photoresist pattern, associated with the irradiation of the electron beam, it is effective to reduce the electron beam irradiation density.

In this embodiment, in order to ensure highly accurate length measurement by suppressing such shrinkage of a sample that causes changes in its shape due to electron beam irradiation as seen in the ArF photoresist, the scan area on the sample surface is formed as a set of multiple scanning lines and when the shape and dimensions of the sample surface are measured using either a straight line connecting the starting and ending points of the dimension to be measured or the scanning distance of the convergent electron beam on scanning lines adjacent to the straight line, the scanning line interval can be set so as not to exceed such certain irradiation density value of the focusing electron beam on the surface of the sample that is dictated by the physical characteristics of the sample surface material.

In this embodiment, consideration is also given so that when the measuring points are to be observed and when the field of view is to be searched for, the distance and interval of scanning lines at which the aspect ratio of the sample image becomes 1 to optimize the observation are set, and when measurements are to be performed, the scanning line interval is set so as not to exceed the above-mentioned certain irradiation density value on the surface of the sample, and so that as a result, the scanning line interval during the measurements does not exceed the scanning line interval during the observation. That is to say, for measurement, the ratio of the scanning line interval value with respect to the length of the scanning lines is increased above the ratio to be applied to observation and to the search for the field of view.

In addition, the scan width of the scanning lines and the interval thereof can be set for the conditions that minimize the amount of shrinkage of the ArF photoresist pattern due to the electron beam, and after combinations of these values have been registered as fixed values beforehand, these combinations can be selected when measurements are to be performed. Description is given below using drawings.

Figure 2A:
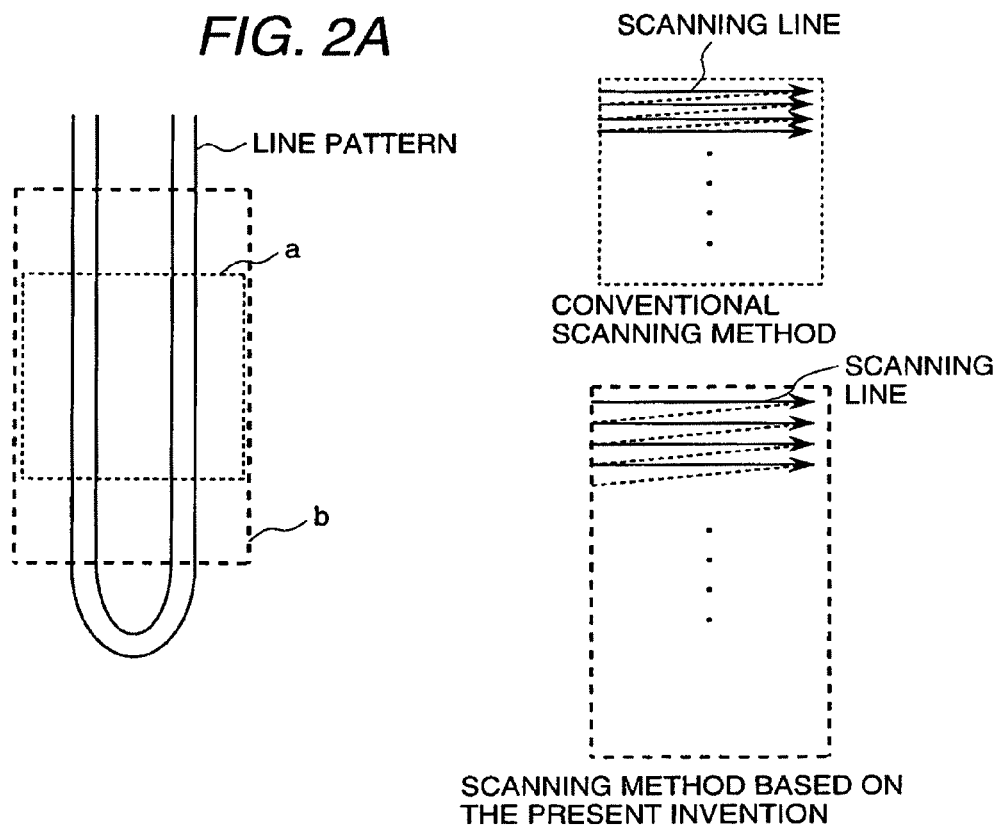
FIG. 2 is a view explaining the method of scanning with an electron beam during the measurement of a line pattern dimension, subject to the prevent invention.
Figure 2B:
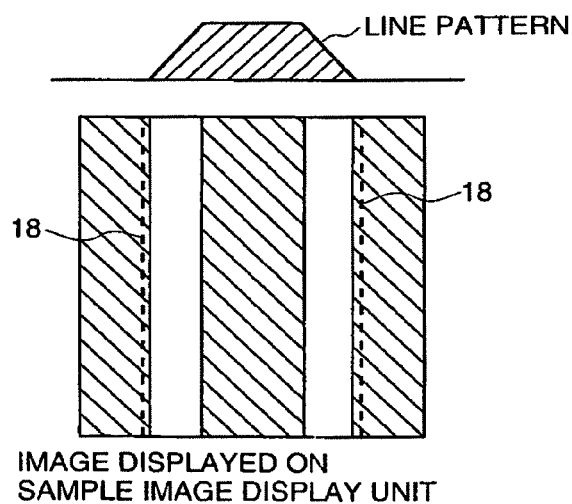
Figure 2C:
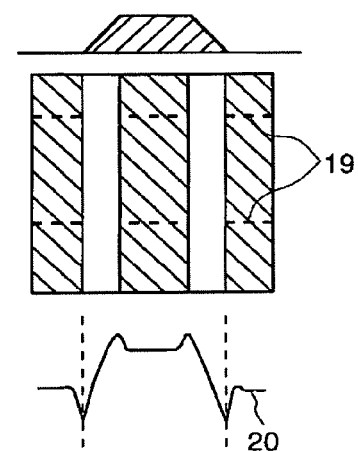

The method of electron beam scanning during pattern dimension measurement in the present invention is shown in FIG. 2. FIG. 2(*a*) is for a pattern of a linear shape. Under the prior art, for the observation and measurement of a sample image, the length and interval of the scanning lines are controlled so that the magnifications in the vertical and horizontal directions of the sample image take the same value with high accuracy, and for this reason, scans are conducted in the square area shown as "a" in the figure. Under this method of electron beam scanning, however, as the micropattern size becomes smaller, since the image magnification must be increased to maintain measuring accuracy, this results in the electron beam scanning square area becoming smaller, thus increasing the electron beam irradiation density per unit area. Accordingly, for a sample whose physical and chemical changes are caused by the irradiation of the electron beam, such as a sample that suffers shrinkage as in the ArF photoresist, there occurs the problem that according to formula (1) shown above, the irradiation of the electron beam causes dimensional changes in the pattern and this prevents dimension data from being measured accurately or stably.

Next, the shrinkage of the ArF photoresist is described. Since the shrinkage of the ArF photoresist occurs when the electron beam that has entered the photoresist collides with and are scattered about the photoresist molecules, the shrinkage generally increases with increases in the energy of the electron beam. Therefore, for the scanning electron microscope that measures the secondary electron generated from the sample, it is known that since the primary electron beam usually stops inside the sample (in this case, the ArF photoresist), the shrinkage will increase as the acceleration voltage of the primary electron beam increases and as the quantity (current density) of electron beams entering the ArF photoresist increases. In other words, since, even with the same quantity of electrons, increases in measuring magnification reduce the electron beam irradiation area, the quantity of electrons entering the same area correspondingly increases and shrinkage progresses.

Next, the shrinkage of the photoresist due to its mutual action against the electron beam is outlined using FIG. 4. In FIG. 4 (1), the primary electron beam, after entering the ArF photoresist, repeats colliding with and scattering about the photoresist over range R and then stops. In FIG. 4 (2), when electron beams enter one after another, the photoresist area affected by the electron beams will shrink. However, not all the section affected by the electron beams will shrink. Instead, the shrinkage will occur only according to the rate of change of the parameter K1 determined by the photoresist. The new electron that has entered will affect the photoresist that has shrunk, the photoresist that has not shrunk even though it has been affected by the previous electron, and a new photoresist that has not been affected by the previous electron, and in this way, new shrinkage is caused. The discontinuous line in the figure denotes the position of the photoresist existing before it shrunk. In FIG. 4 (3), the area where the shrinkage occurred and the range of the electron beam have matched to terminate the shrinkage.

In the prior art, although the shrinkage of photoresists due to the irradiation of electron beams has been achievable only by reducing the quantity of electron beams or the measuring magnification, there have been the problems that the S/N ratio of the secondary electron signal decreases or that reduction in the magnification deteriorates measuring accuracy and/or repeatability.

For these reasons, under the present invention, control and arithmetic unit 30 controls the scanning signal of the deflecting coil 11 by use of deflecting coil control power supply 24, and further provides control to maintain the distance of scanning lines in a direction orthogonal to the line pattern to be measured (in the case of FIG. 2(*a*), in the direction of the horizontal axis) while at the same time maintaining the image magnification in a horizontal direction, and to broaden the interval of scanning lines in the direction of the line pattern (in the case of FIG. 2, in the direction of the vertical axis) and thus reduce the image magnification in this direction, with the result that electron beam scanning occurs in the rectangular scan area shown as "b" in the figure. Hereby, since the electron beam irradiation density per unit area is reduced, changes in the dimensions of the ArF photoresist due to the irradiation of the electron beam are suppressed. This, in turn, not only enables highly accurate measurement of the dimension, but also enables measurement without the deterioration of measuring accuracy since the magnification in the horizontal direction of the sample image does not decrease.

At this time, the pattern the dimension can be calculated by arranging two cursors at the secondary electron beam displayed on the image display unit and then performing arithmetic operations from the image magnification and the cursor-to-cursor distance by use of control and arithmetic unit 30. Or measurement data can be calculated by displaying a profile 20, which can be obtained by adding in a vertical direction the profile of the horizontal signal intensity in the section existing between two horizontal cursor lines 19, and then detecting the edge of the pattern from the profile 20.

Figure 3A:
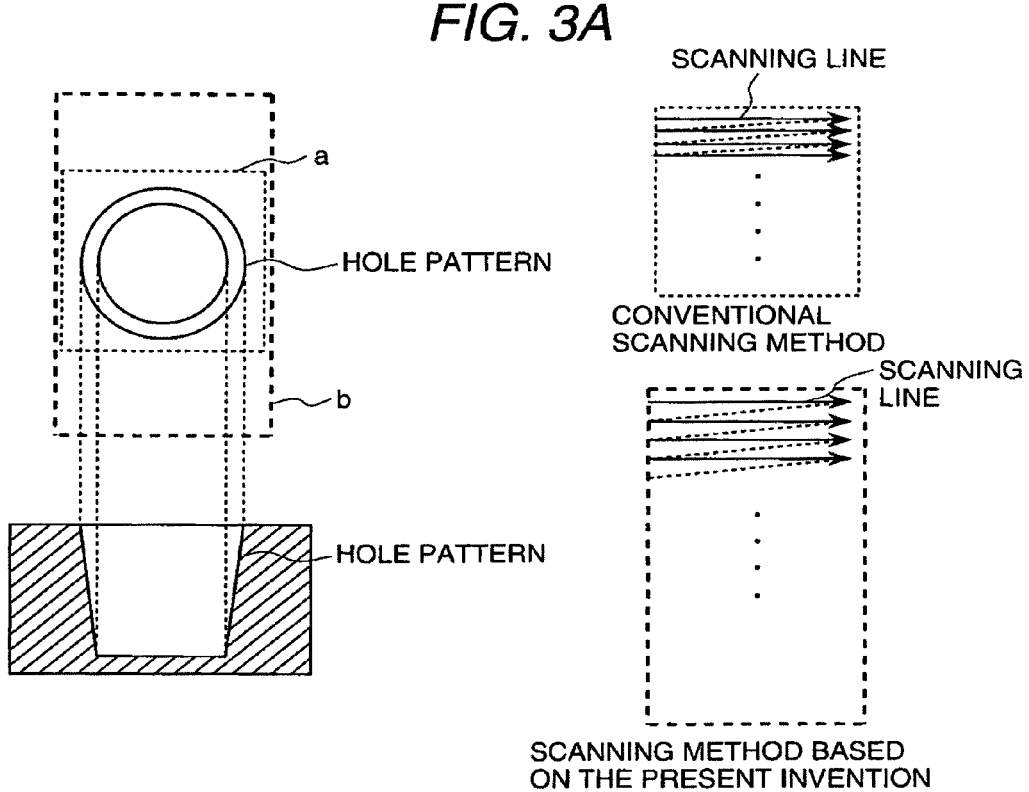
FIG. 3 is a view explaining the method of scanning with an electron beam during the measurement of a hole pattern dimension, subject to the prevent invention.

FIG. 3 shows electron beam scanning intended to measure a hole pattern of a hole shape. For the prior art, a square scan area surrounding the intended hole is scanned with an electron beam and the hole pattern also needs to be increased in image magnification according as the hole diameter is reduced. This, in turn, increases the electron beam irradiation density, posing the problem that the photoresist shrinks.

Even in this case, under the present invention, control and arithmetic unit 30 controls the scanning signal of the deflecting coil 11 by use of deflecting coil control power supply 24, and further provides control to maintain intact the distance of the horizontal scanning lines for measuring the dimension on the image of the sample while at the same time maintaining the image magnification in the horizontal direction, and to broaden the interval of scanning lines in a direction vertical to the dimension measuring direction. Hereby, the electron beam irradiation density can be reduced and highly accurate measurements with minimum changes in dimension can be performed without measuring accuracy being affected.

Figure 3B:
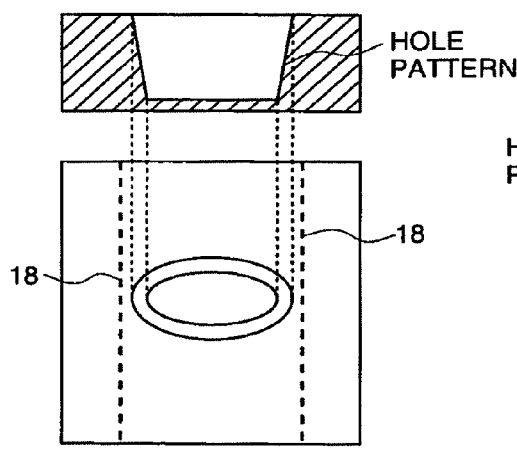
Figure 3C:
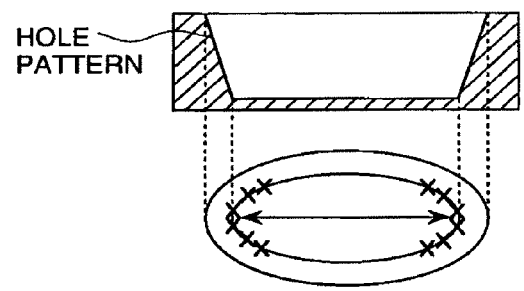

At this time, although the image shown in FIG. 3(b) is formed by electron beam scanning in the scan area mentioned above, it is allowed either to arrange two cursors at the top of the elliptic image displayed on the image display unit and measure the diameter of the hole, or as shown in FIG. 3(c), to detect the left and right edges in a multipoint format, then approximate the respective curves, and measure the hole diameter at the position where the distance between the left and right curves becomes a maximum.

Another embodiment is possible. More specifically, although its configuration is the same as that of FIG. 1, the distance and interval of the scanning lines for observing the sample image and or searching for the measuring points can be set so that the magnification is the same between the vertical and horizontal directions of the sample image and so that only when measurement is specified from input unit 27 by the operator, can the length and interval of scanning lines be set to values suitable for the sample and greater than the interval for observation. It is possible by doing so to supply the operator with a natural operating environment free from a feeling of uneasiness and to improve the ease in operations.

Yet another embodiment is also possible. More specifically, although its configuration is also the same as that of FIG. 1, when the sample to be measured is an ArF photoresist, the distance and interval of the scanning lines for the measurement can be set beforehand from the irradiation current value at which the shrinkage of the ArF photoresist becomes a maximum.

Figure 5:
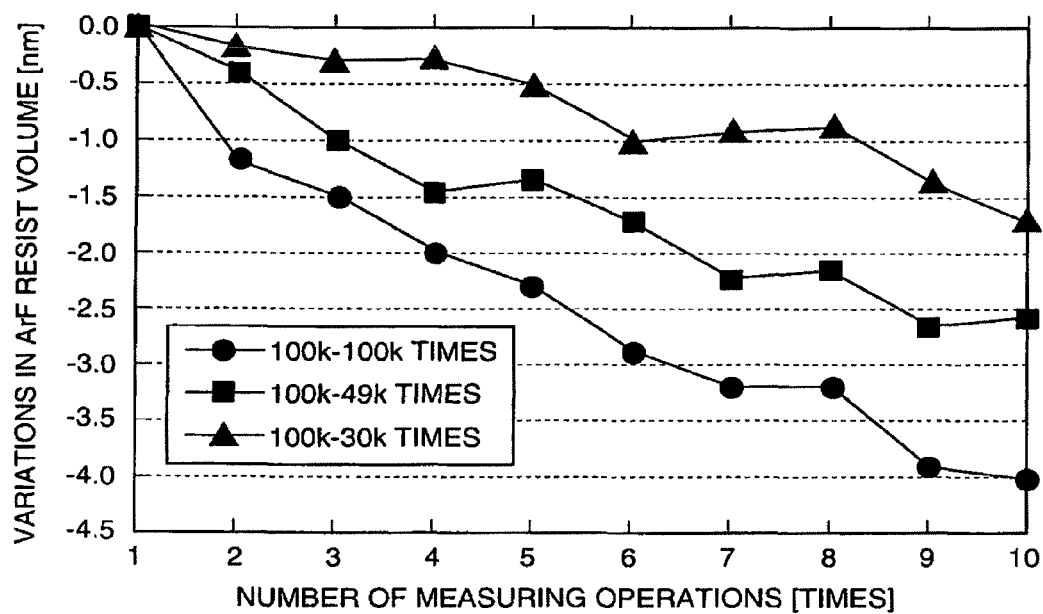
FIG. 5 is a diagram showing the relationship between the number of measuring operations and the amount of shrinkage.

The results of the experiments which have been conducted by the inventors by use of an ArF photoresist to represent the relationship between the number of measuring operations and the amount of shrinkage are shown in FIG. 5. In the semiconductor manufacturing process that uses an ArF photoresist, the line widths of patterns are limited to 0.1 µm or less and to measure patterns of these line widths, image magnifications must be at least 100 k times as great. In this case, an acceleration voltage of 300 V and a probe current value of 4 pA are used and the number of frames to be added is four. The horizontal and vertical magnifications of the sample image which can be measured in FIG. 5 without the deterioration of measuring accuracy during scanning based on the prior art are 100 k times by look times, under which conditions, the total amount of shrinkage which has occurred during 10 measuring operations was about 4 nm.

Under the present invention, when the horizontal and vertical magnifications of the sample image were set to 100 k by 49 k and 100 k by 30 k as the conditions for reducing the electron beam irradiation density by broadening the interval of scanning lines for a wider scan area, the respective amounts of shrinkage were about 2.5 nm and 1.6 nm.

It can be judged from the above that when an ArF photoresist with a line width of 0.1 µm is to be measured, setting the horizontal image magnification to 100 k times and minimizing the electron beam irradiation density are preferable. Actual operation is also restricted according to the vertical length of the pattern to be measured.

Figure 7:
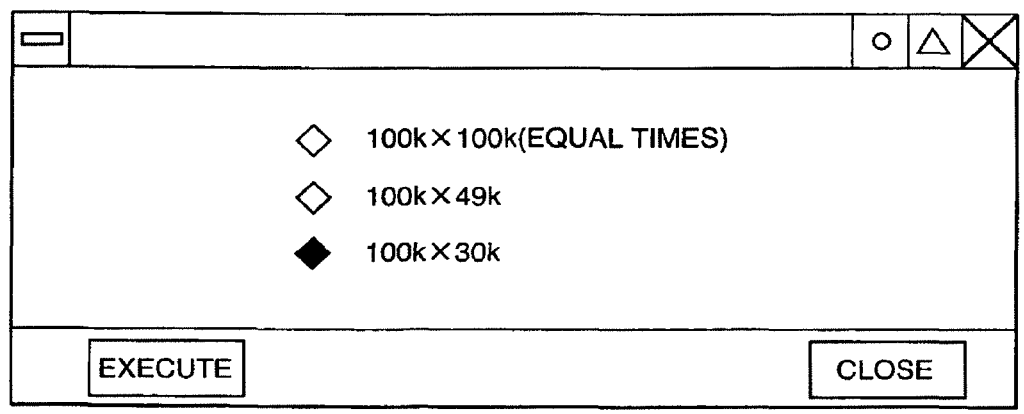
FIG. 7 is a view showing an example of a magnification selection screen mode.
Figure 6:
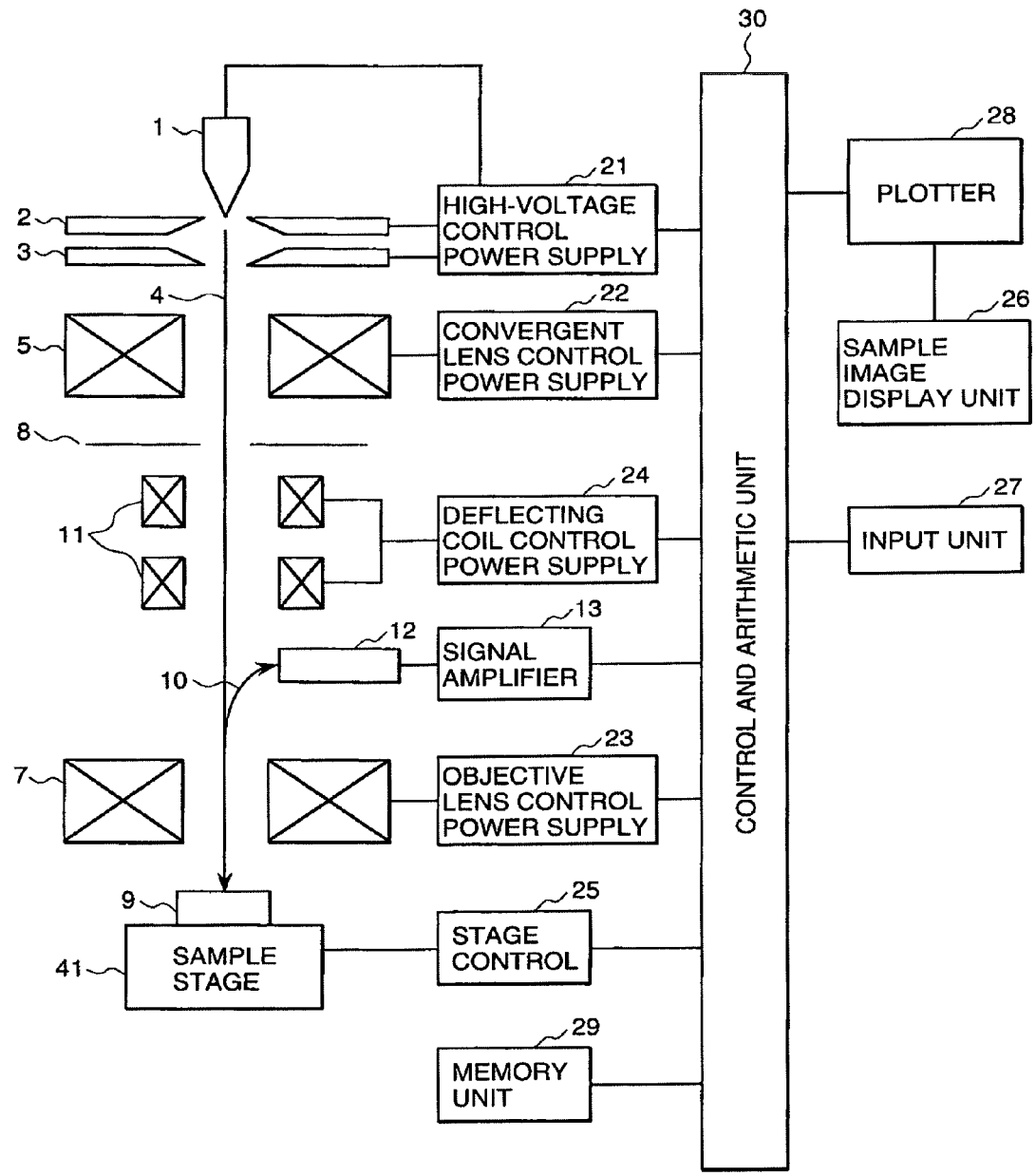
FIG. 6 is a block diagram of the scanning electron microscope shown as another embodiment of the present invention.

FIG. 6 shows yet another mode of embodiment, wherein control and arithmetic unit 30 is equipped with a memory unit 29 so that combinations of the optimal conditions for measuring the sample can be stored as fixed values. To the operator, there is the advantage that measurements suitable for the sample can be easily performed within a short time by selecting conditions from the combinations when measuring the dimensions of the sample. FIG. 7 shows an example of a related selection screen mode, wherein the operator can easily perform measurements in a new scan area by starting the measuring function after selecting conditions suitable for the sample which is to be measured, from the combinations of fixed image magnifications that are displayed on the screen.

According to this embodiment of the invention, in the case of measuring such a photoresist that changes in shape by the action of the electron beam irradiated for observing the sample, variations in shape can be minimized and highly accurate and stable measurement of the dimension is possible.

Also, operational convenience improves since the observation of the sample and the search for the field of view of the section to be measured can be facilitated by selecting a normal square scan area for the observation.

In addition, there is the advantage that since combinations of the scanning line length and interval matched to the characteristics of the sample are registered beforehand, the optimal measuring conditions can be easily set by selecting the desired combination.

Figure 24:
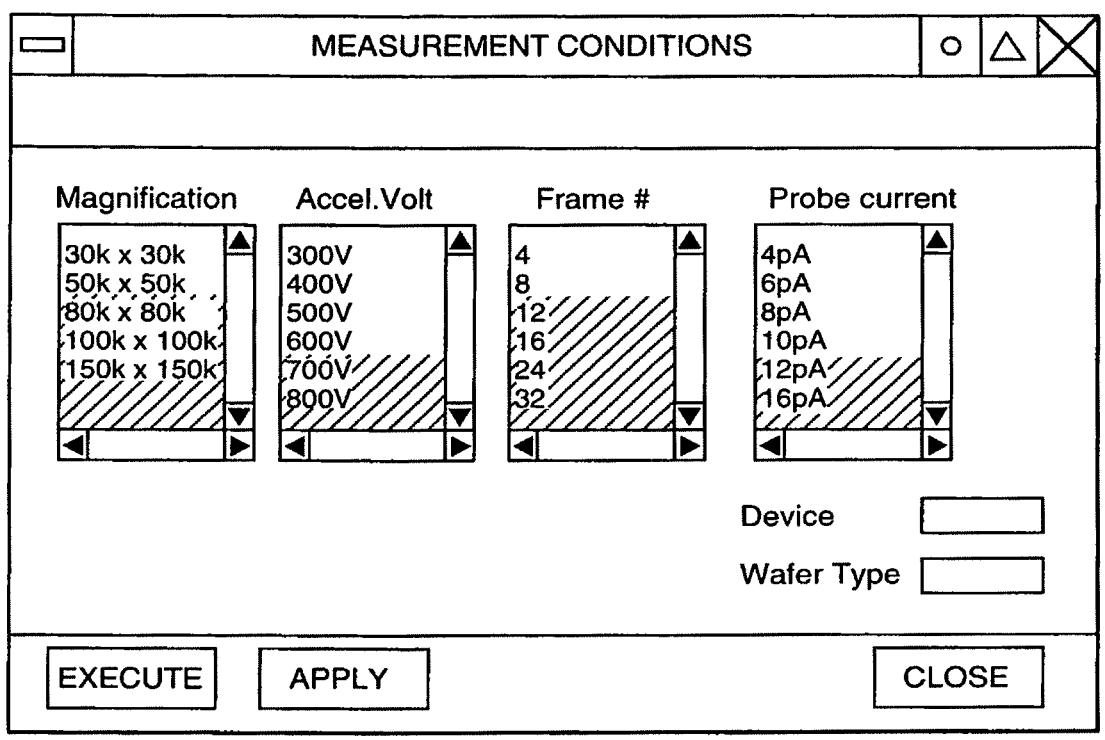
FIG. 24 is a diagram explaining an example of the screen mode for setting the optical parameters for the scanning electron microscope.

FIG. 24 is a diagram explaining an example of the screen mode for setting the optical parameters for the scanning electron microscope. In this screen mode, it is possible to set at least the electron beam acceleration voltage (Accel. Volt), the probe current, the magnification, and the total number of frames (Frame#) necessary to form one frame image. Control and arithmetic unit 30 controls each optical element, subject to the data settings in the above-mentioned setting screen mode. In the example of FIG. 24, data that can be set as the acceleration voltage, the probe current, the magnification, and the total number of frames, and actual data settings greater than the above data that can be set are displayed so as to be identifiable.

For example, for the selection of the total number of frames, a selection field consisting of permissible values such as 4, 8, 12, 16, 24, and 32, is provided so that the operator can select the appropriate total number of frames. In the example of FIG. 24, although only 4 or 8 can be selected from the above permissible values, the selection of 12, 16, 24, 32, and so on up to the maximum permissible value is not accepted.

For the apparatus pertaining to this embodiment of the invention, the required value is set beforehand as the maximum amount of shrinkage and there is also incorporated a sequence in which, when at least one optical parameter is set in accordance with formula (1), other permissible parameter data will be calculated and entry of data greater than the permissible parameter data will be inhibited. According to this apparatus configuration, adequate observing conditions can be specified with shrinkage reduced to its minimum.

Also, although an example of inhibiting entry of data greater than the permissible parameter data has been explained in the description of the above-described embodiment, this embodiment is not limited by the explanation of the example. For example, if data greater than the permissible parameter data is entered, the appropriate message can be displayed on the display unit or an audio warning can be issued. It is thus possible to notify to the operator that the settings of the remaining parameters are in excess of the respective required values.

Embodiment 2

Figure 8A:
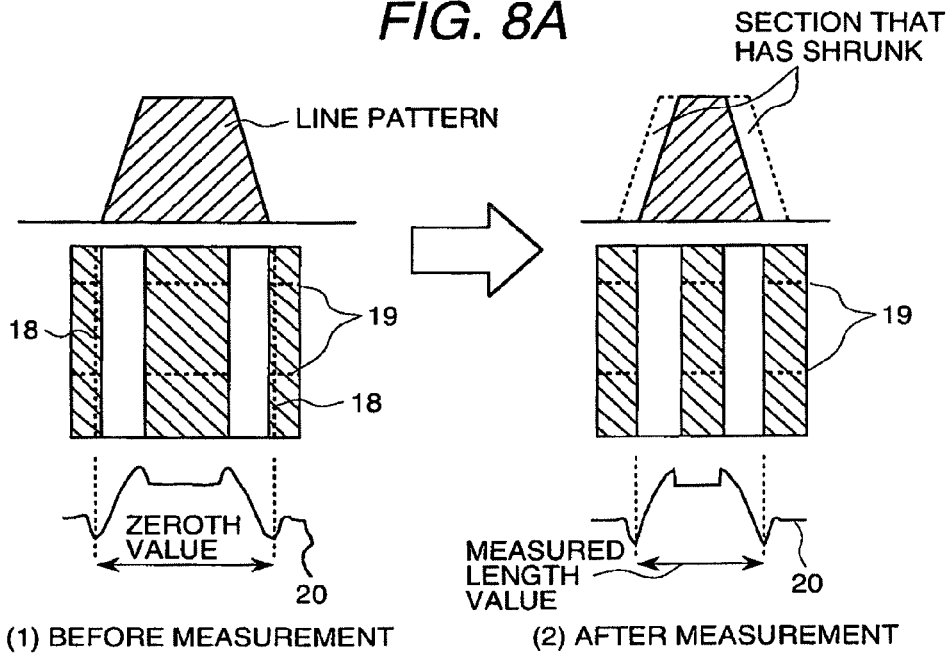
FIG. 8 is a diagram showing the relationship between zeroth measured data and actually measured data.
Figure 8B:
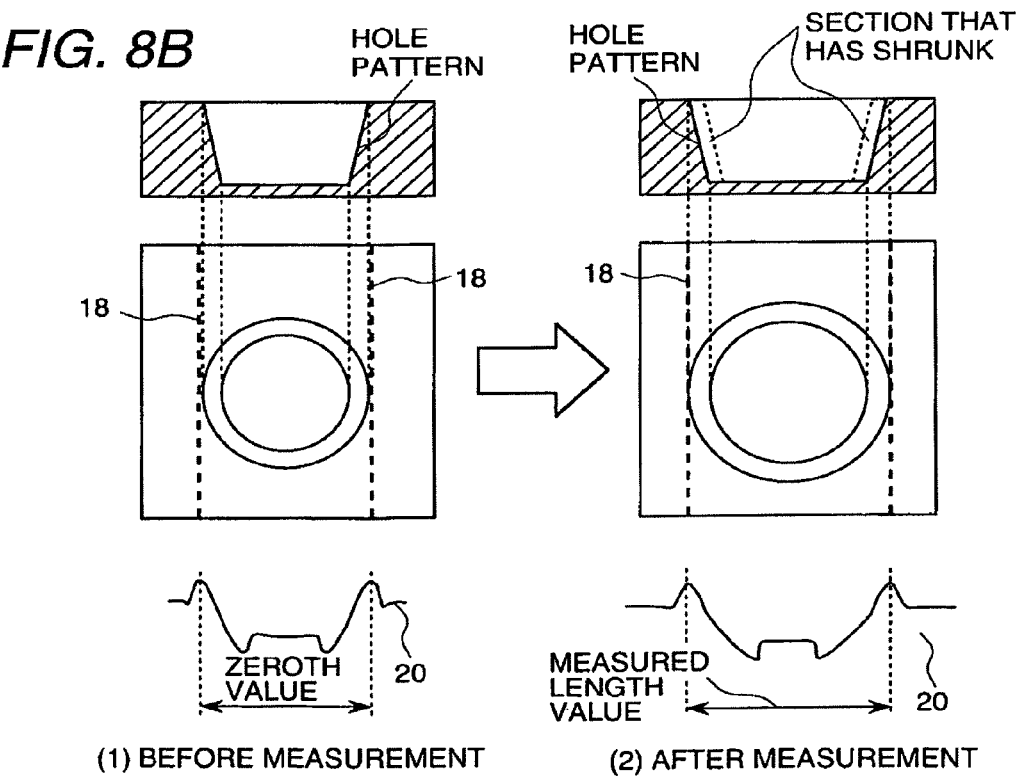

For a semiconductor device, in order to achieve its design performance, the shape and dimensions of its circuit pattern requires stringent management and for this purpose, a length-measuring electron microscope capable of measuring microdimensions is used during their inspection process. During observing and measuring processes, however, electron beam irradiation for length measurement changes the shape of the pattern, as shown in FIGS. 4 (1) to (3). If this pattern is a line pattern, the length value measured will be smaller than the dimension before it is measured, as shown in FIG. 8($a$). If the pattern is a hole pattern, conversely, the length value measured will be larger than the dimension before it is measured, as shown in FIG. 8($b$), and this will create the problem that the dimension existing before shrinkage occurs cannot be detected.

There is also the problem that when one section is continuously measured, since line width is varied by the repetition of electron beam irradiation, different data measurement results are created with each measuring operation and as a result, measuring accuracy does not improve. Since the pattern shrinks according to length, the accurate dimension value of the pattern cannot be detected and this is a major bottleneck in the semiconductor device manufacture that uses the ArF photoresist.

The art disclosed in Japanese Application Patent Laid-Open Publication No. Hei 09-166428 is intended to reduce any effects of contamination on measurement by deriving approximate curves from a plurality of measuring operations and then estimating the dimensions of the sample existing before electron beam irradiation. However, no consideration is given to the fact that shrinkage progresses with an increase in the number of measuring operations.

Also, at semiconductor factories, in order to evaluate the stability of measuring equipment, one section is measured 10 times in succession and measured data is reduced in dispersion. However, since shrinkage progresses according to the particular electron beam irradiation level, the repetition of length measurement at one point causes pattern shrinkage, increases measured data in terms of dispersion (3σ: σ is the standard deviation of measured data), and creates problems associated with process management.

In this embodiment of the invention, description is given of a length measuring method suitable for measuring the length of a pattern whose shrinkage cannot be avoided, and an apparatus for conducting the length measurement.

As described earlier in this Specification, the shrinkage of the ArF photoresist pattern is likely to be a chemical reaction due to the energy of the convergent electron beam entering the photoresist. It can also be seen from formula (1) that as the number of measuring operations ("n") is increased, the amount of shrinkage (2S) will gradually decrease and the shrinkage itself will eventually cease.

In addition, the measured data itself decreases with each measuring operation and eventually converges to a fixed level at which the shrinkage does not progress any further. These changes in measured length data, plotted for the number of measuring operations, are shown in FIG. 9($a$), and it can be seen from FIG. 9($b$) that approximation with the function of ⌐┴ is possible. This approximation function is a function showing how the pattern dimension changes (decreases).

Therefore, as can be seen from FIG. 9($c$), the dimensions of a pattern before its shrinkage is caused by length measurement can be obtained by calculating the approximation function from the length data that has been obtained as a result of a plurality of pattern measurements, and then providing the above approximation function with zero-point extrapolation. The approximation function at this time can be of high order or it can be a linear approximation function when the number of measuring points is small. In the statement below, the estimated length value of the pattern before it shrinks is described as the "zeroth value" in the meaning of the length value obtained by the zeroth measurement based on the electron beam.

In this embodiment, in order to ensure measuring accuracy for such sample suffering a change in shape due to electron beam irradiation as seen in the ArF photoresist, and achieve the objects described earlier in this Specification, the multiple length values that have been measured at one measuring point using such a scanning electron microscope as set forth in FIGS. 1 and 6 are stored into a memory first. Next after an approximation function has been calculated from these measured length values, the approximation function is extrapolated and the dimensions of the ArF photoresist existing before an electron beam is irradiated are calculated.

Furthermore, up to now, the stability of a length measuring apparatus, especially, repeatability has been evaluated with 3σ, the dispersion between the length values that were obtained by repeating measurements 10 times at one section. However, for such a sample deformed by electron beam irradiation as in the ArF photoresist, measured length data varies, regardless of the characteristics of the length measuring apparatus. Consequently, the obtained 3σ value has not always indicated changes in the characteristics of the length measuring apparatus.

In this embodiment, as shown in formula (2) below, after the first zeroth length value (hereinafter, called the zeroth value) has been calculated from an "m" number of length measurements, the (m+n)th measurement is performed and the second zeroth value is calculated from the (m+n) number of length data measurements. In this way, the third zeroth value, the fourth zeroth value, and so on up to the last zeroth value are obtained from the (m+n) number of length data measurements, the (m+3) number of length data measurements, and so on up to the (n) number of length data measurements, respectively. Furthermore, the accuracy of each of the zeroth values can be improved by setting "m" to the appropriate value, and as measured data is chronologically newer, the magnitude of the data to be used for estimation will increase, with the result that the zeroth values will improve in accuracy and reliability.

It is also possible, by enabling the evaluation of the dispersion between the 10 zeroth values which have thus been obtained, to improve measuring accuracy in comparison to evaluating the dispersion of the length value itself which changes with each measurement, and thus to reduce the total dispersion. At this time, any number of zeroth values can also be selected to evaluate dispersion.

$$M_{0,1} = \text{Fit}(M_1, M_2, \ldots M_m)$$

$$M_{0,1} = \text{Fit}(M_1, M_2, \ldots, M_m, M_{m+1})$$

$$\ldots \quad (2)$$

$$\ldots$$

$$\ldots$$

$$M_{0,n} = \text{Fit}(M_1, M_2, \ldots, M_m, \ldots, M_{m+n-1})$$

where "$M_{0,n}$", "$M_m$", and "Fit( )" denote the nth zeroth value, the mth measured length value, and the approximation function that has been fitted to the selected value of all measured length data, respectively.

The desired zeroth value can be calculated from at least one measuring operation by acquiring and storing into a memory beforehand the approximation function that has been obtained above, and then using this approximation function when length is measured. Prior calculation of the function that denotes changes in the pattern dimension due to electron beam irradiation makes it unnecessary to continue the electron beam irradiation for the calculation of the approximation function, and as a result, damage to the pattern which shrinks can be minimized.

This approximation function can be selected from the multiple approximation functions that have been calculated and registered beforehand for the sample which is to be measured. Or the amount of energy to be given to the sample under the current conditions during measurement can be provided with internal interpolation from the acceleration voltage, the probe current, the observing magnification, the number of electron beam scans, and other approximation functions that have been calculated beforehand for the maximum/minimum electron beam energy applicable to the sample, and these approximation functions can be combined and the results can be used to estimate the zeroth value. Once an actual length value has been obtained, the thus-obtained approximation functions are shifted horizontally for matching to the results of one measuring operation, through such processes as shown in FIGS. 21(a) to (c), and the zeroth value corresponding to the acquired length value is estimated.

With reference to the energy of the electron beam entering the sample and variations in the shape and dimensions of the sample, since a change of the acceleration voltage ($V_{acc}$) changes the energy itself of the electron beam, an increase in $V_{acc}$ also increases the energy applied to the sample and, hence, variations in the shape and dimensions of the sample. Since increasing the current density ($I_p$) increases the irradiation current density and increasing the observing magnification (MAG) reduces the electron beam irradiation area inside the sample, the amount of current irradiation per unit area is augmented and the energy irradiated will also increase. Also, increasing the number of electron beam scans (Frame) for an improved S/N ratio by increasing the quantity of signals from the surface of the sample increases the energy given thereto in proportion to the number of scans.

Figure 13A:
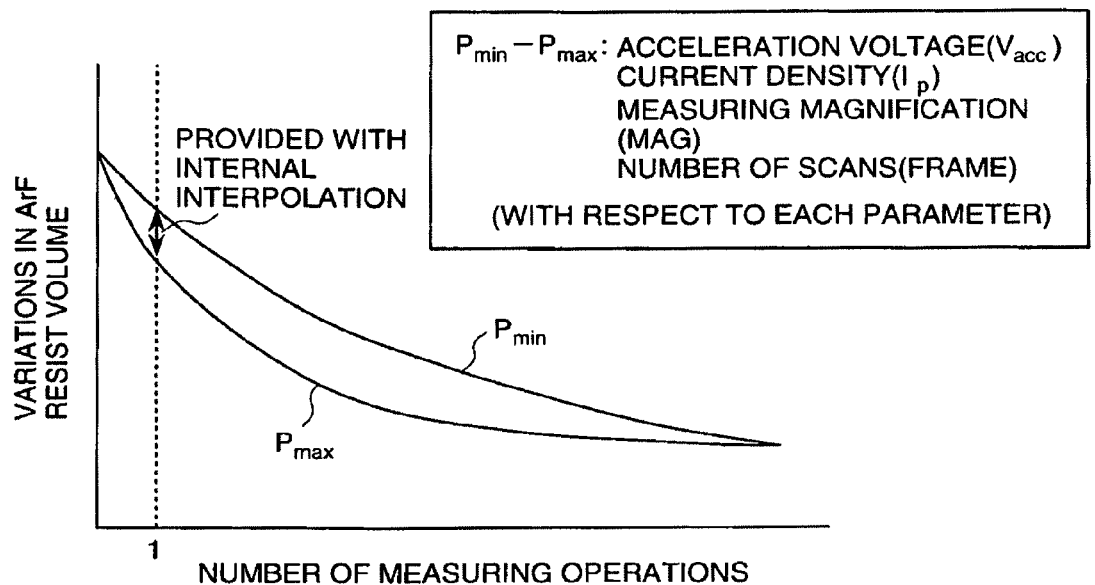
FIG. 13 is a diagram showing an internal interpolation process.
Figure 13B:
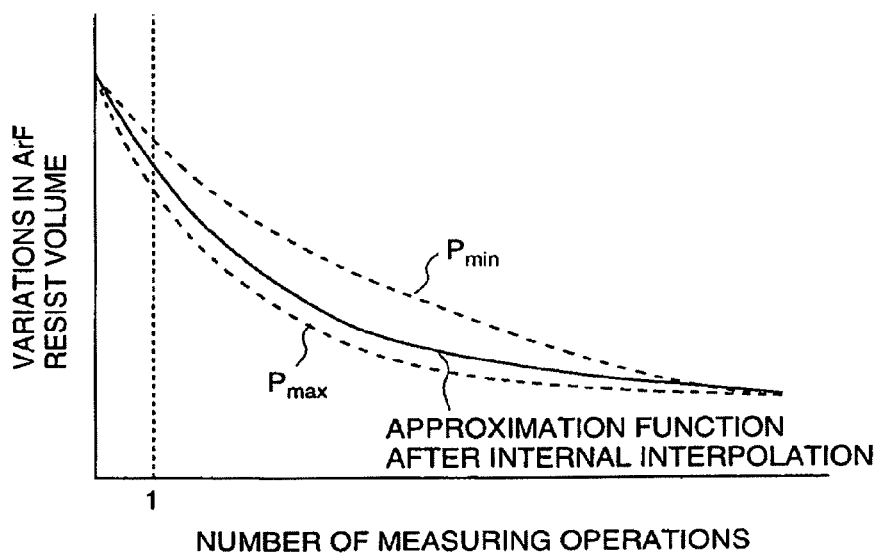

Therefore, the approximation functions existing when the respective parameters are maximal/minimal are calculated beforehand and then the internal interpolation matching to the particular length-measuring conditions is provided so that the zeroth values corresponding to each parameter can be calculated. At this time, as shown in FIGS. 13(a) to (c), the approximation functions for the maximum ($P_{MAX}$) values and minimum ($P_{MIN}$) values of parameters such as the acceleration voltage which can be applied to the sample, the current density, the observing magnification, and the number of scans, are calculated and stored into a memory beforehand, and then the approximation functions obtained by internally interpolating each such parameter for each measuring operation are combined to obtain the approximation function corresponding to the current irradiation energy. The thus-obtained approximation function is shifted horizontally in the axial direction of measured length data in FIG. 13, then matched to the results of one length measurement, and the zeroth data corresponding to the irradiation energy is estimated. The above optical parameters can be arbitrarily set from, for example, input unit 27, and control and arithmetic unit 30 controls each optical element of the scanning electron microscope in accordance with the instructions sent from input unit 27. Electron beam scanning can be either one-dimensional or two-dimensional.

By the way, as shown in formula (3), the final variation in the volume of the sample "$\Delta_{total}$" can be calculated and output as the difference between the zeroth value and the final measured value by calculating the zeroth value from the approximation function.

$$\Delta_{total} = M_{0,T} - M_{m+T-1} \quad (3)$$

where $M_{0,T}$ and $M_{m+T-1}$ denote the final zeroth value and measured length value, respectively. Furthermore, as shown in formula (4), the difference $\Delta_n$ between the nth zeroth value $M_{0,n}$ and the (m+n−1)th measured length value $M_{m+n-1}$ can be calculated each time a measuring operation is performed.

$$\Delta_n = M_{0,n} - M_{m+n-1} \quad (4)$$

Or instead of calculating variations as shown above, it is possible to continuously execute length measurement at one measuring point with respect to the variation X in any sample volume that was entered from the input unit, and continue the measuring process until the Δ shown in formula (4) above has overstepped the range of X. That is to say, formula (5) can be added as a measuring condition.

$$|\Delta_n| < X \quad (5)$$

When calculated $|\Delta_n|$ exceeds X, he measuring process will be terminated, and the calculated zeroth data, dispersion 3σ between measured data, variation Δ in the volume of the sample, and a graph showing changes in these parameters will be displayed. It is also possible to select not only Δ, but also other parameters (for example, dispersion 3σ between measured data), as the parameters in formula (5) above.

Although the electron microscope is an apparatus that irradiates electron beams from its vacuum vessel to the sample to be measured, it is known that if the molecules of a carbon polymer or of other substances are present in the vacuum vessel, these molecules will react with the sample and accumulate as impurities (hereinafter, called "contamination") on the sample when electron beams are irradiated. In the present invention, since length measurement is continuously executed at one measuring point, when electron beam irradiation is continued even after the shrinkage of the ArF photoresist has ceased, length data measured subsequently will increase according to the quantity of contamination proportional to the electron beam irradiation energy.

Figure 11A:
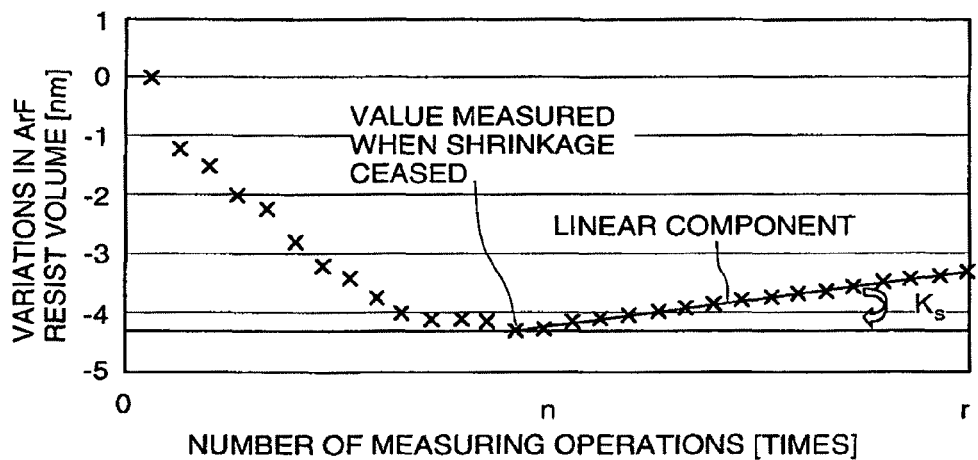
FIG. 11 is a diagram showing the process for calculating zeroth measured data when impurities are present.
Figure 11B:
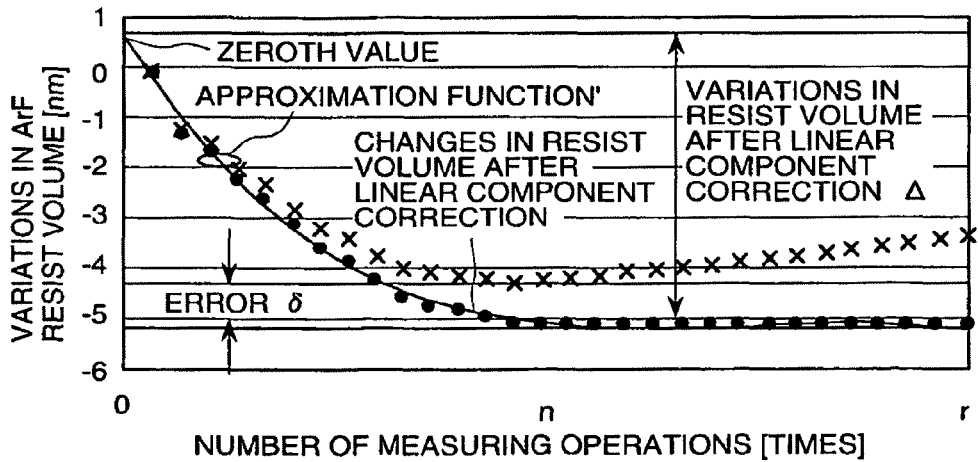

When measurements are continuously performed at one measuring point, the gradient ($K_s$) of the linear component is calculated as in formula (6) after the tendency of measured data to increase has been confirmed. The quantity of contamination which has stuck to the sample during the measuring process at up to that time can be calculated using formula (7).

$$K_s = (M_r - M_n)/(r-n) \qquad (6)$$

$$C = K_s \cdot r \qquad (7)$$

where "r", "n", "C", "$M_r$", and "$M_n$" denote the number of measuring operations, the number of measuring operations in which the shrinkage ceased, the quantity of contamination which has stuck to the sample, the rth measured value, and the nth measured value, respectively. Whether the tendency of measured data has changed to an upturn can be judged as follows. That is to say, the rth measured value and the average ("$M_{ave, r}$") of all data down to the (r−5)th measured value are calculated and stored into a memory. The rth measured value is compared with the previous average value of ("$M_{ave, r-1}$") to confirm the difference between both values. If comparison results indicate a plurality of times in succession that the rth measured value is greater, the shrinkage of the photoresist will be judged to have ceased, as shown in FIG. 11(a). The data section that has increased is estimated to be due to the contamination of the carbon-based substances linearly sticking to the sample during the electron beam irradiation. For this reason, the gradient ($K_s$) of the increase section in the graph is calculated, then after, as shown in FIG. 11 (b), the value ($M_m'$) obtained by subtracting the linear component from the measured data "$M_m$" has been calculated and memory-stored, the approximation function allowing for the quantity of contamination is calculated, and it therefore becomes possible to calculate the zeroth value ($M_{0, n}''$), dispersion between measured data, a variation (Δ) in the volume of the sample, and the like, from the above results and thus to perform measurements with even higher accuracy.

$$M_m' = M_m - K_s \cdot m \qquad (8)$$

$$M_{0,n}'' = \text{Fit}(M_1', M_2', \ldots, M_{m+n-1}') \qquad (9)$$

$$\Delta'' = M_{0,n}'' - M_{m+n-1}' \qquad (10)$$

This embodiment of the invention is described in detail below using flowcharts.

As shown in FIGS. 8 (a) and (b), for pattern dimension measurement, two vertical cursor lines 18 or two horizontal cursor lines 19 are displayed together with an image of the sample on the sample image display unit 26, then the two cursors are placed at the edges of two sections on the pattern via input unit 27, and control and arithmetic unit 30 calculates the measured data as the dimension data of the pattern, from the information consisting of the image magnification of the sample image and the distance between the two cursors, and stores the results into the memory unit. After length measurement has been continuously repeated, sequential calculation results on measured data are stored into the memory unit and the approximation function is calculated by control and arithmetic unit 30. Control and arithmetic unit 30 calculates the zeroth data from this approximation function in accordance with formula (2) and stores the results into the memory unit. The calculated zeroth data can also be displayed on sample image display unit 26.

Length measurement results on the line pattern of the ArF photoresist dealt with in the present invention, and related zeroth data are shown in FIG. 8. Originally, before electron beams are irradiated, the pattern width shown as the "zeroth value" in FIG. 8 (1) is measured as the after-measurement width in FIG. 8 (2) from the line profile within the range specified by the horizontal cursor lines 19 of the line pattern, since the irradiation of the electron beam causes the ArF photoresist to shrink and the line profile to change.

Figure 9A:
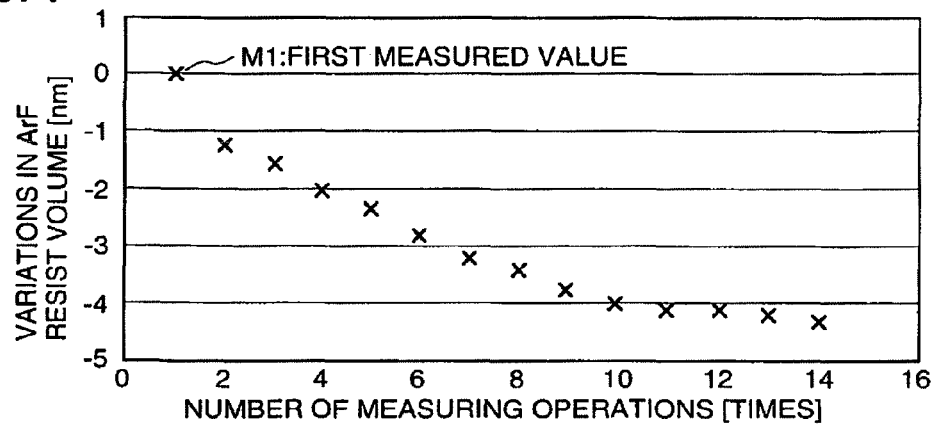
FIG. 9 is a diagram showing the calculation process for zeroth measured data.
Figure 9B:
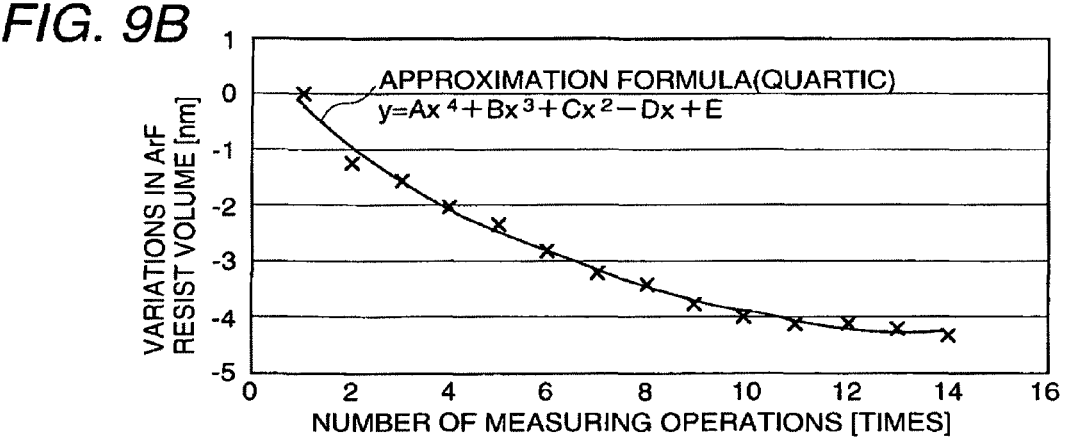
Figure 9C:
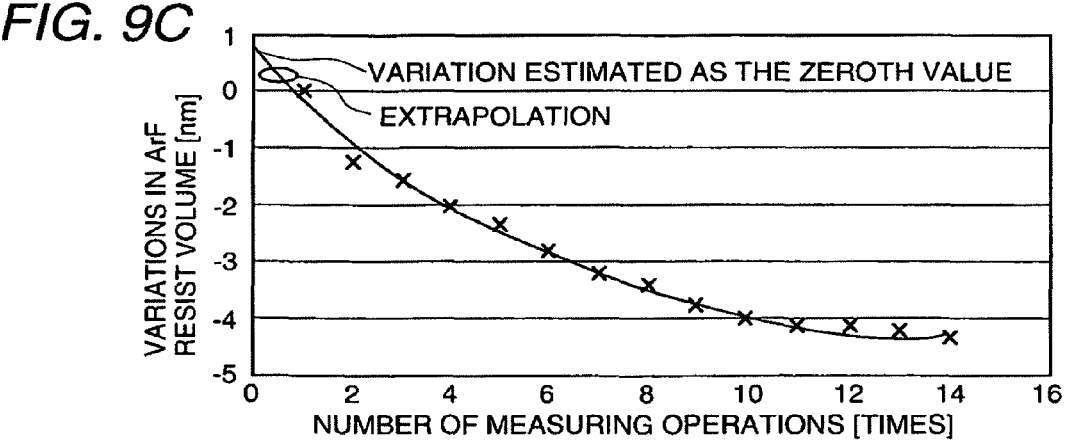
Figure 10:
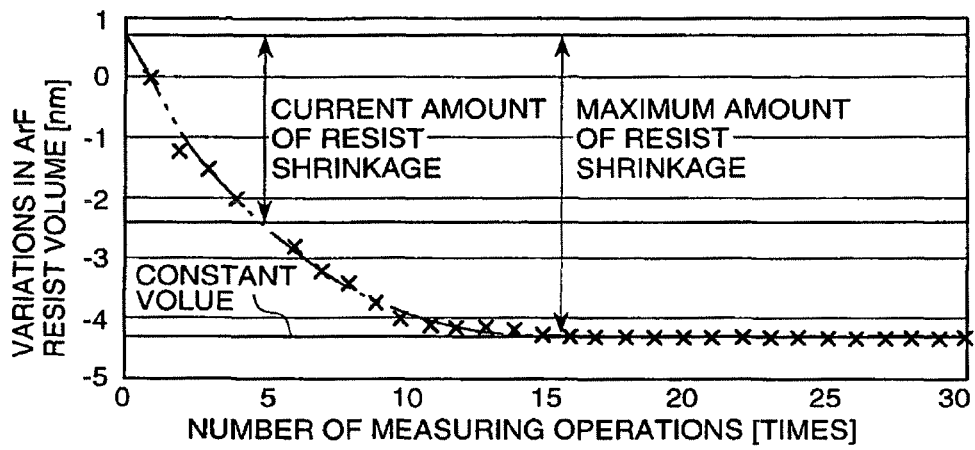
FIG. 10 is a diagram showing the relationship between the number of measuring operations and the amount of shrinkage.
Figure 14:
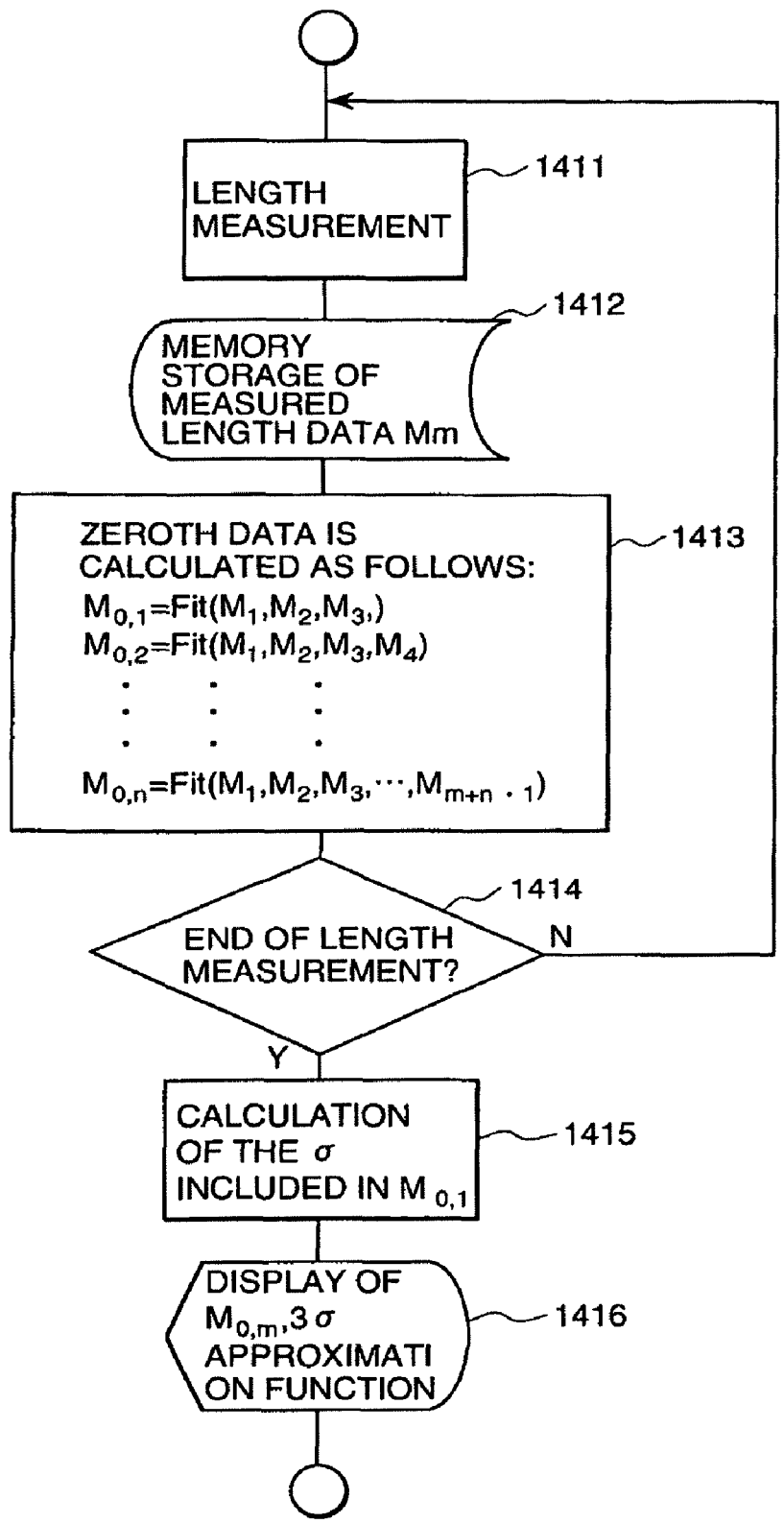
FIG. 14 is a diagram showing the measuring process for zeroth measured data.

Further details of this embodiment are described below using the conceptual diagram of FIG. 9 in line with the flow diagram of FIG. 14. In step 1411, the length of the intended pattern on the sample is measured, and in step 1412, the measured value is stored into the memory unit. The value at this time is stored as the value corresponding to the first measuring point ($M_1$) in FIG. 9(a). Following this measuring operation, the measuring process is repeated at the same measuring point, and the respective measurement results are stored as measured length values $M_2$, $M_3$, and so on up to $M_m$. As shown in FIG. 9(b), the measured length data approximation functions with respect to the number of measuring operations is calculated from the "m" number of length measuring points for an "m" number of length measurements by control and arithmetic unit 30 (FIG. 9(b) shows an example of approximation with a quartic formula, and in FIG. 14, "m" is taken as 3). Next as shown in FIG. 9(c), the zeroth value $M_{0,1}$ is calculated by providing the zeroth measurement with extrapolation and the results are memory-stored. When the length measuring process is further continued, approximation functions are sequentially calculated from an (m+1) number of measuring points, an (m+2) number of measuring points, and so on up to an (m+n−1) number of measuring points, in step 1413, and the zeroth data is calculated and stored. Following completion of the length measuring process in step 1414, an "n" number of zeroth values, approximation functions, data dispersion (3σ), and other data will be displayed on display unit 26 in step 1416.

Also, ten zeroth values are calculated by the arithmetic unit similarly to the above. After this, the standard deviation σ is derived from the ten calculated zeroth values $M_{0, 1}$, $M_{0, 2}$, $M_{0, 3}$, and so on up to $M_{0, 10}$, and 3σ, which is obtained by multiplying σ by three, is calculated and displayed as an index denoting the stability of the length measuring apparatus. Thus, data on the stability of the length measuring apparatus can be calculated and displayed without being affected by changes in the volume of the sample due to electron beam irradiation. The calculation of the standard deviation from the thus-obtained zeroth values enables the accuracy of the apparatus to be easily confirmed when length measurements are performed on such micropatterns (100 nm or less) as formed by the photoresist reacting to argon fluoride (ArF) eximer laser light.

Figure 15:
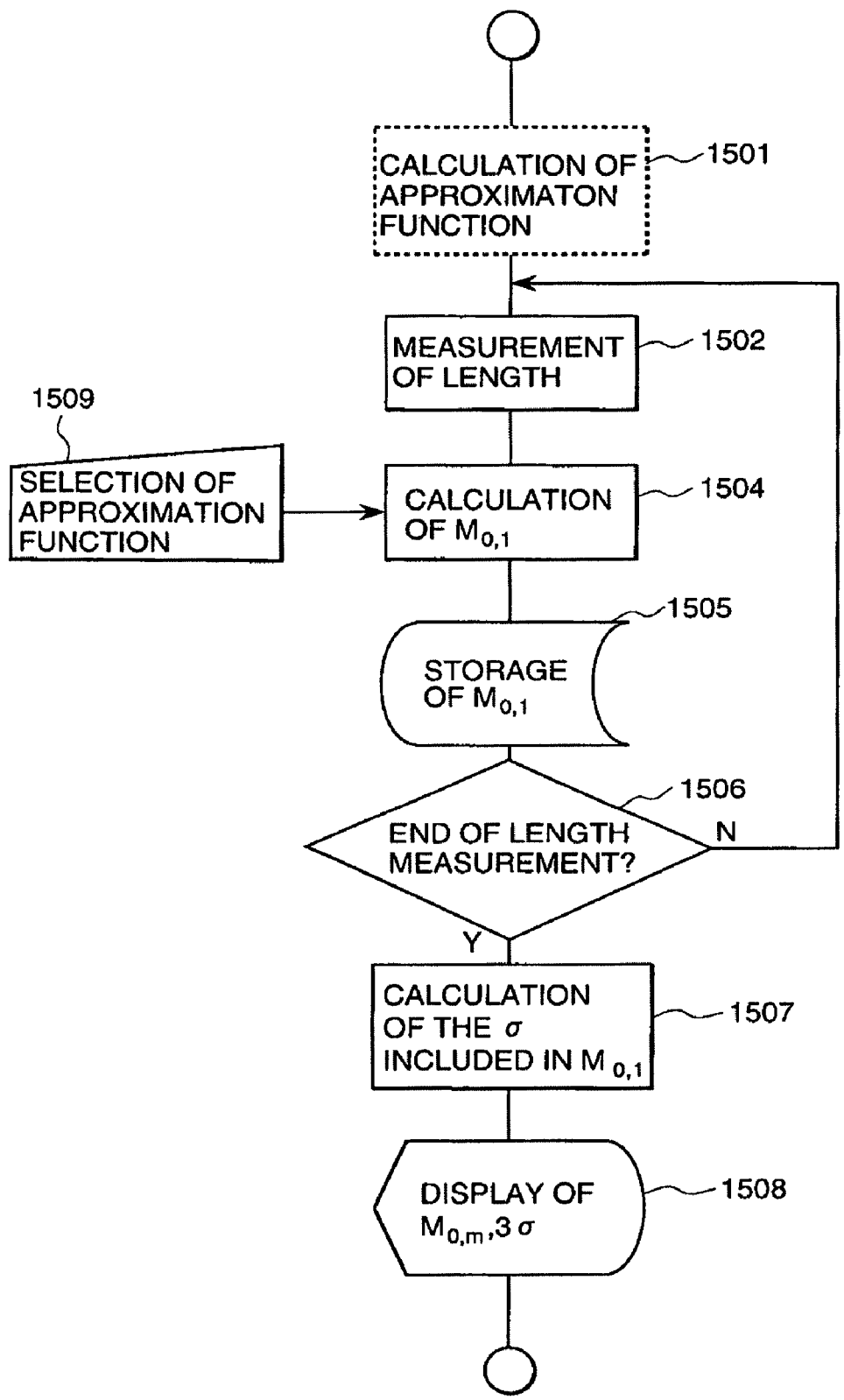
FIG. 15 is a flowchart showing the process in which an approximate function is to be stored into a memory beforehand and zeroth measured data is to be calculated from the results of at least one measuring operation.

Next, an example of storing approximation functions beforehand and calculating zeroth values from the results of one length measuring operation is shown below using the flow diagram of FIG. 15.

In cases such as conducting automatic length measurements on a plurality of samples using a length measuring electron microscope and one recipe, the approximation functions that were obtained similarly to the above-described embodiment are stored beforehand in step 1509, then the zeroth value $M_{0, 1}$, is calculated from the results of one length measuring operation that were obtained in step 1502, by providing corrections using the above-mentioned approximation functions, as shown in FIGS. 21(a) to (c), and the results are stored into the memory unit in step 1505. After the lengths of the multiple samples have been measured, dispersion 3σ between the zeroth data, which is the measurement results, is calculated and stored in step 1507 and the zeroth values and data dispersion of each sample are displayed on display unit 26. The data at this time can be displayed with each calculation of the zeroth value. Also, the approximation functions used can be such that as shown in step 1509, they have been acquired beforehand using one sample, or such that as shown in step 1501, they have been obtained in the range of automatic length measurement. It is possible, by adopting such composition, to calculate zeroth values with at least one measuring operations and thus to minimize the shrinkage of the pattern whose length is to be measured.

Figure 16:
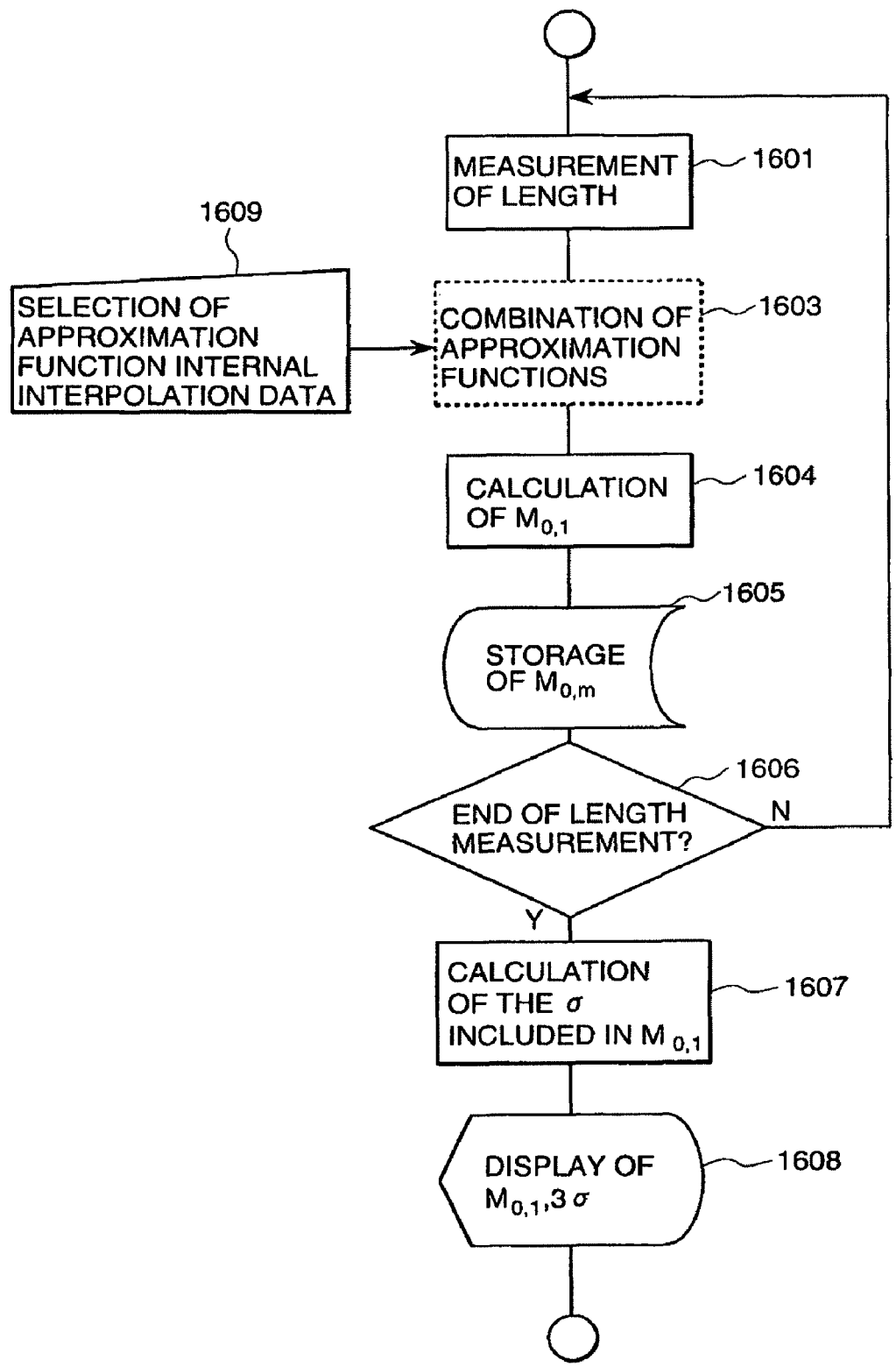
FIG. 16 is a flowchart explaining the process for estimating zeroth measured data from a previously calculated approximate function and from the optical conditions of the scanning electron microscope.

Next, an example of zeroth data estimation based on the approximation functions that have been calculated beforehand, and on the optical conditions of the electron microscope, is described using the flow diagram of FIG. 16. In the case of automatic length measurement of a plurality of samples by use of a recipe, in step 1609, the approximation functions $P_{max}$ and $P_{min}$ obtained when the parameters for changing the energy of electron beams to be applied to each sample (namely, acceleration voltage: $V_{acc}$, current density: $I_p$, measuring magnification: MAG, and the number of electron beam scans: Frame) are maximal and minimal are calculated by control and arithmetic unit 30 and calculated data is stored into the memory unit. Since the data varies from sample to sample in terms of the type of photoresist material and the shape of the pattern, data matching the type of sample needs to be acquired and stored and the appropriate data for the intended sample is to be selected from acquired and stored data.

Measured length value $M_1$ is acquired and stored in step 1601, then in step 1603, the approximation functions obtained during one length measuring operation when the $P_{max}$-$P_{min}$ section is internally interpolated are, as shown in FIG. 13(b), calculated from the current parameter status and stored by control and arithmetic unit 30. After this, as shown in FIG. 13(c), the calculated and stored approximation functions are further combined and stored as the approximation functions for the estimation of zeroth data.

Figure 20A:
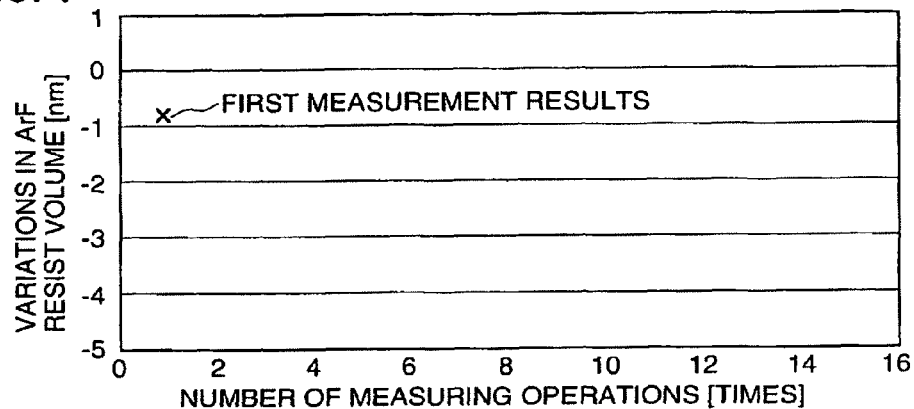
FIG. 20 is a diagram explaining the screen mode for selecting an approximation scheme.
Figure 20B:
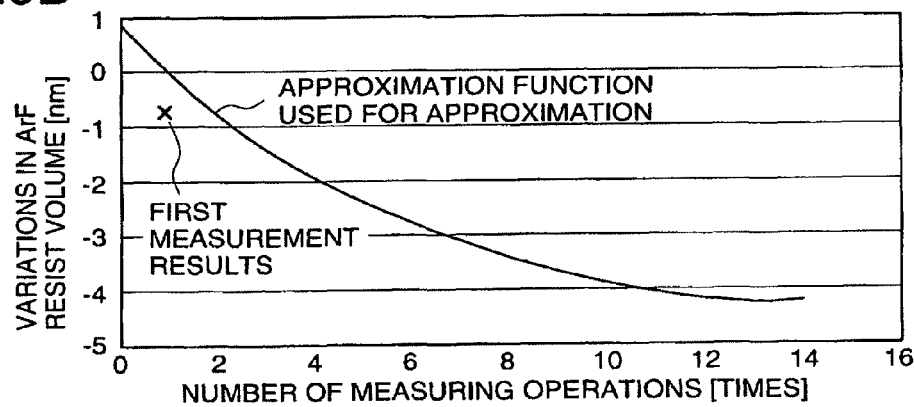
Figure 20C:
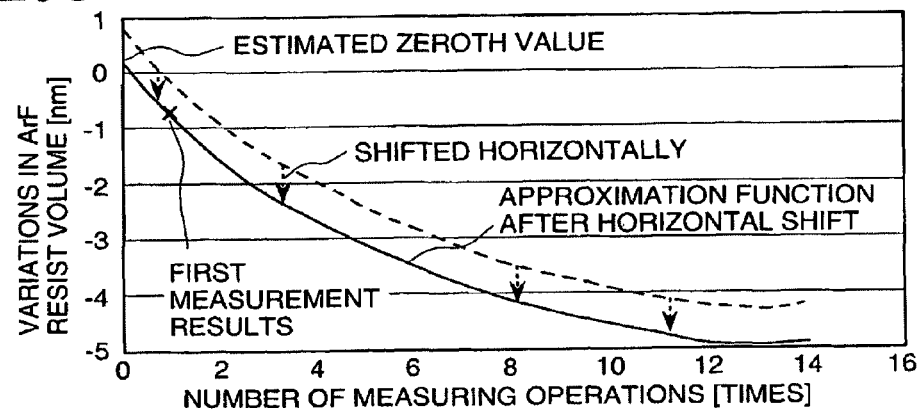

When the current irradiation conditions are maintained in the length measuring process, correction coefficients can be calculated by checking these coefficients against the length measuring energy conditions each time the measurement is conducted, or the coefficients that have thus been calculated can be used to calculate zeroth value $M_{0, 1}$ during subsequent measuring operations. After that, in step 1604, approximation functions are calculated from the measured length data that has been stored into the memory unit, and the approximation function obtained by combining the calculated and stored approximation functions is shifted horizontally with respect to each measured length value, as shown in FIGS. 20(a) to (c). Hereby, the zeroth value $M_{0, 1}$ obtained by correcting the quantity of energy irradiation to the sample is calculated and stored.

After all sample length measurements have been completed, dispersion 3σ between a plurality of zeroth values $M_{0, 1}$ is calculated in step 1607 and the plurality of zeroth values $M_{0,1}$ and the dispersion 3σ between these values are displayed on display unit 26 in step 1608. If necessary, the display can be made each time a zeroth value is acquired. Data acquisition in step 1609 can take place in an earlier step or immediately before step 1601.

It is possible, by adopting the composition described above, to calculate the approximation functions matching the optical parameters, and thus to select the appropriate approximation function even after the apparatus conditions have been modified.

Figure 21:
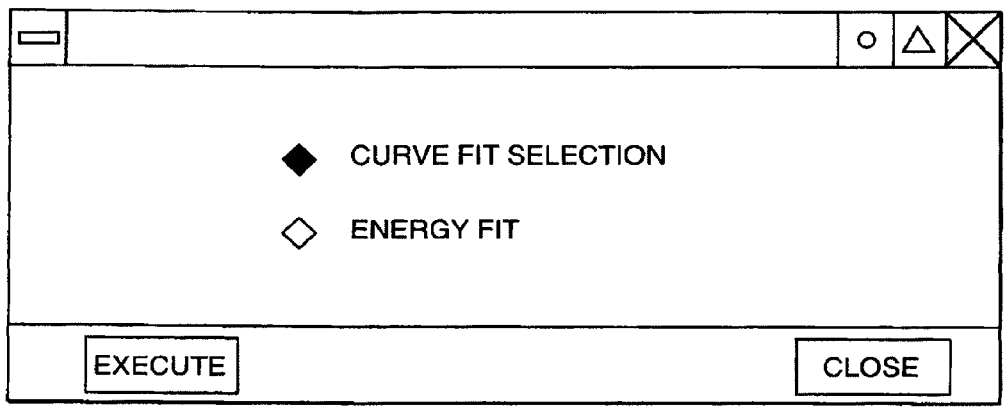
FIG. 21 is a diagram explaining a first example of the screen mode for selecting and supplying an approximation function.
Figure 22:
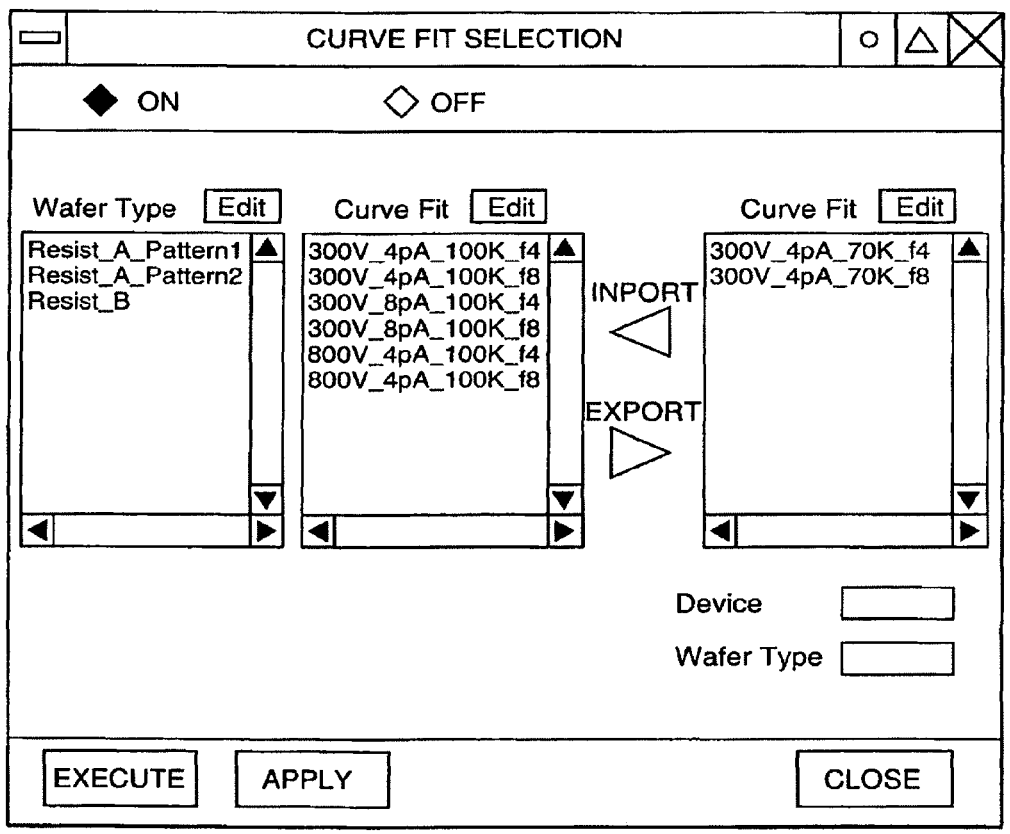
FIG. 22 is a diagram explaining a second example of the screen mode for selecting and supplying an approximation function.
Figure 23:
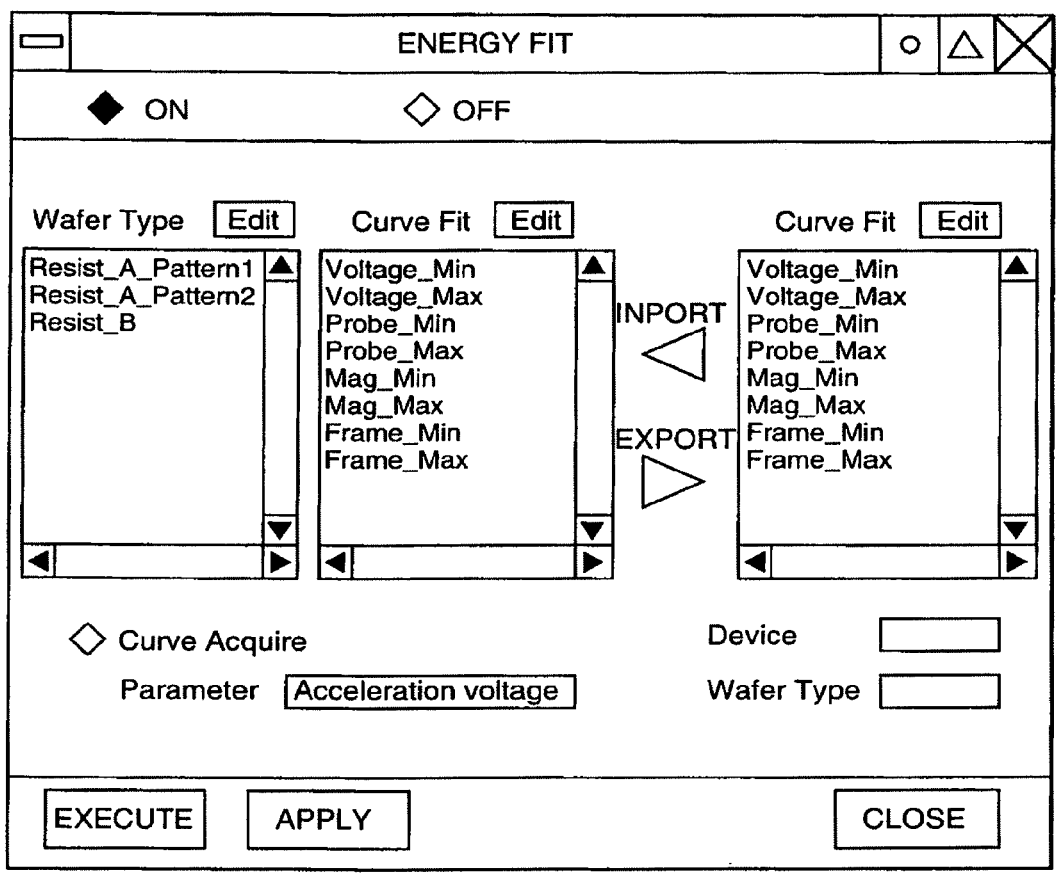
FIG. 23 is a diagram explaining a third example of the screen mode for selecting and supplying an approximation function.

In this embodiment of the invention, such input unit as shown in FIGS. 21 to 23 is provided to enable the operator to arbitrarily acquire and set, or to edit, the approximation function to be used for measurement.

In the input screen mode shown in FIG. 21, the operator can select whether the approximation functions that have been acquired beforehand are to be used to estimate zeroth values, or whether the approximation functions that have been automatically calculated for the incident energy to the sample. Also, the input screen mode shown in FIG. 22 enables the acquisition not only of the approximation functions that have been acquired beforehand, but also of new approximation functions. In addition, the approximation curves separately supplied from the apparatus supplier, manufacturer, and/or the like, can be introduced and these curves can be edited and selected to estimate zeroth data.

Furthermore, in the screen mode of FIG. 23, not only the approximation functions to be used to estimate zeroth data, but also the approximation curves obtained when the acceleration voltage, the electron beam density, the observing magnification, the number of electron beam scans, and other parameters required for automatic zeroth data estimation from the incident energy level are maximal and minimal can be supplied from the apparatus supplier, manufacturer, and/or the like.

Figure 17:
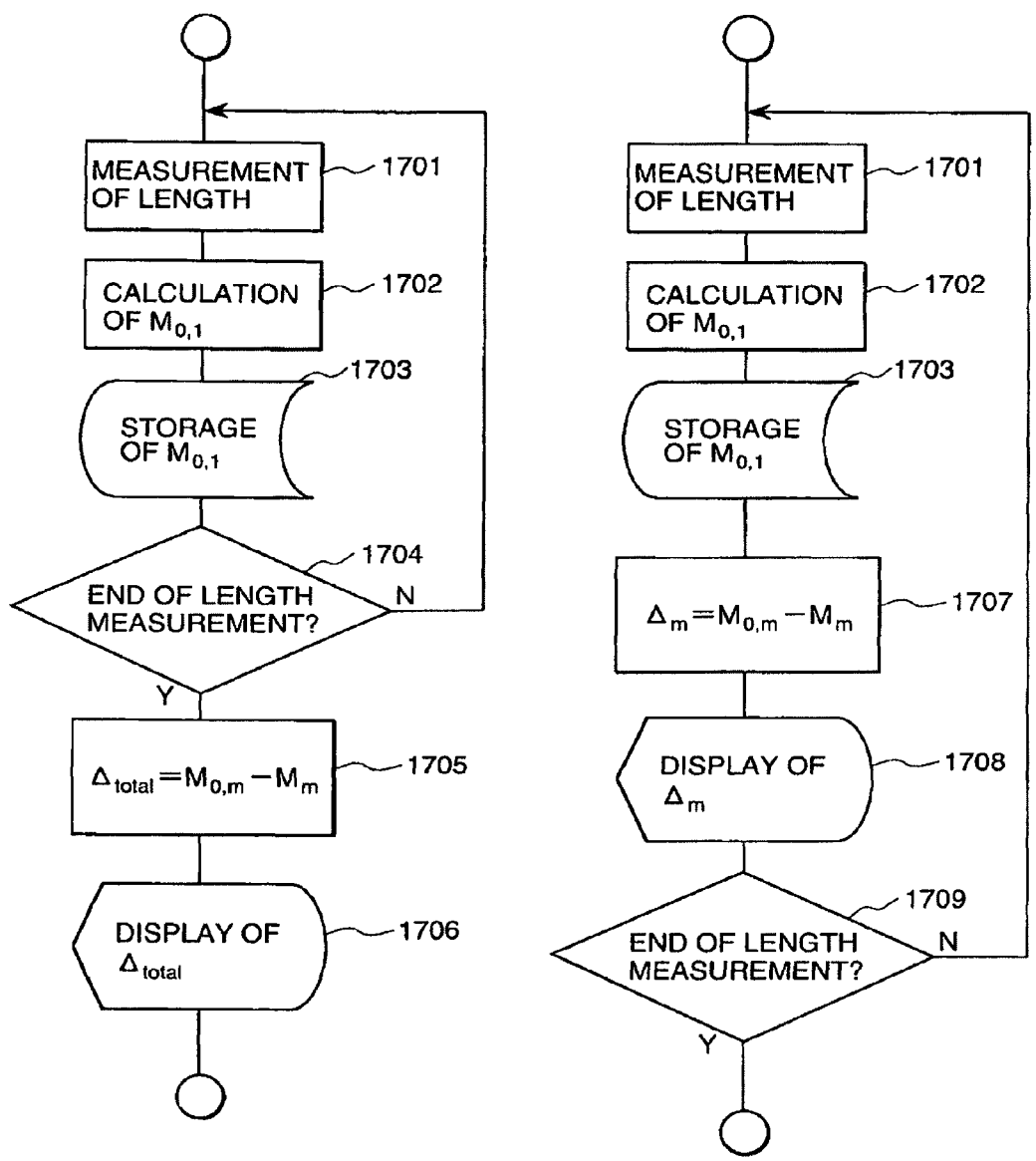
FIG. 17 is a flowchart showing the process for calculating the differences between zeroth measured data and (m+n−1)th measured data.

FIG. 17 is a flowchart showing the process for calculating the difference between the zeroth value and (m+n−1)th measured length value. In steps 1701 to 1704 of FIG. 17(a), measurement at one measuring point is repeated (m+T−1) times, then after approximation functions have been calculated, zeroth data is calculated. Next in step 1705, by use of formula (3), the total variation "$\Delta_{total}$" in the (m+T−1) number of measurement results is calculated from the zeroth value $M_{0, T}$ that has been calculated from the (m+T−1) number of measured length values, and from the (m+T−1)th measured value $M_{m+T-1}$, and calculation results are stored.

In step 1706, the variation "$\Delta_{total}$" is displayed on display unit 26. At this time, the degree of shrinkage can be easily understood by, as shown in FIG. 17(b), calculating and displaying the difference "$\Delta_m$" between the (m+n−1)th zeroth value $M_{0, n}$ and the (m+n−1)th measured length value $M_{m+n-1}$, during each length measuring operation by use of formula (4).

Figure 12A:
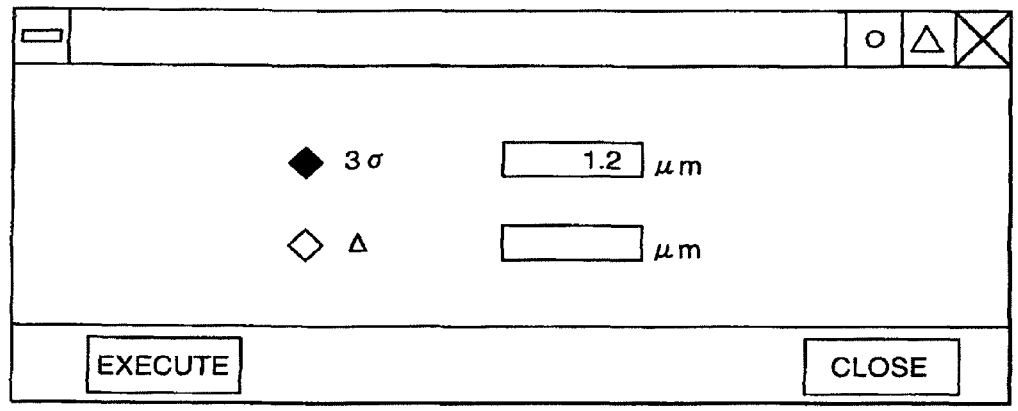
FIG. 12 is a view showing the outline of an input screen mode and measurement.
Figure 18:
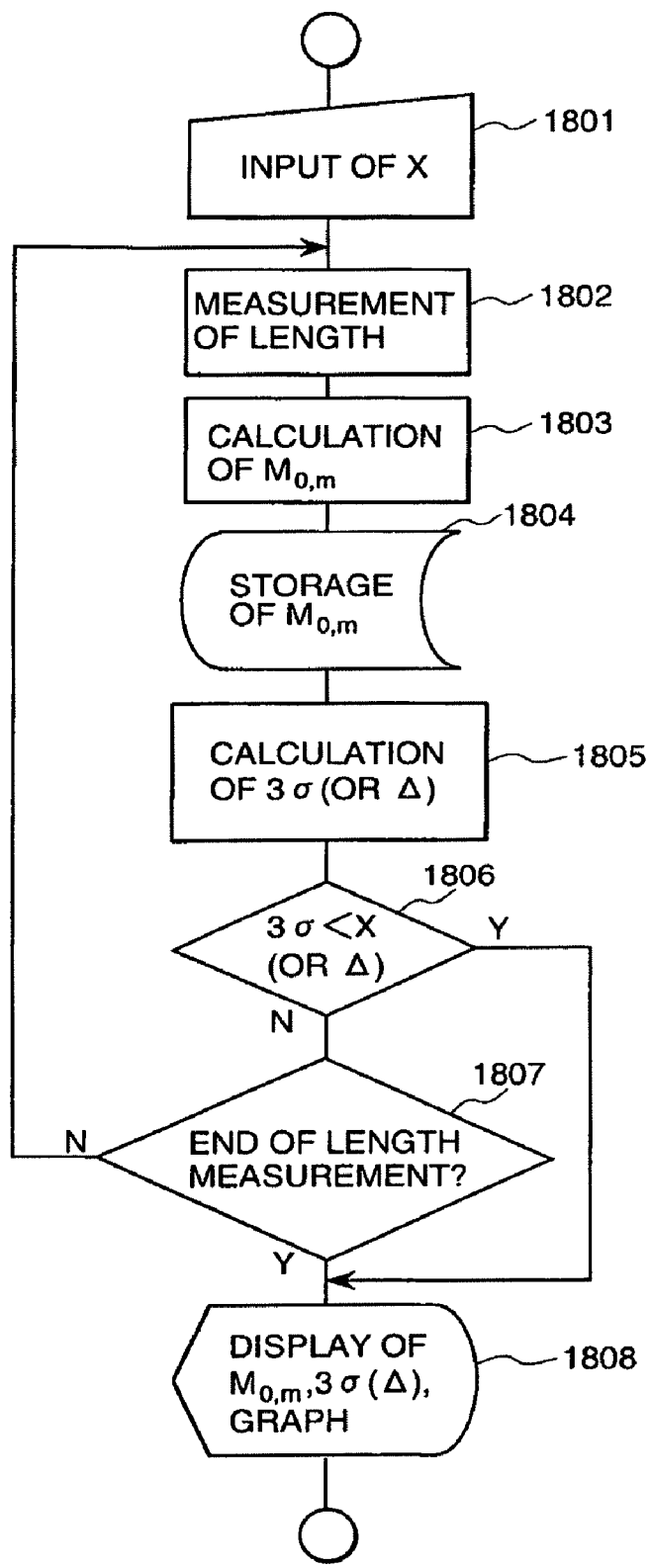
FIG. 18 is a flowchart showing the process for stopping length measurement when the required amount of shrinkage is observed.

FIG. 18 is a flowchart showing the process for stopping the length measuring process when the required amount of shrinkage is detected or when the dispersion in zeroth data decreases below the required value. In step 1801, by use of such input screen mode as shown in FIG. 12(a), the operator can select either the dispersion 3σ of any measured length data or the variation "Δ" in the volume of the sample, and enter a value of X. Subsequently, in steps 1802 to 1804, the current zeroth value $M_{0, n}$ is calculated from the calculated and stored length data that was continuously measured at one measuring point, and then in step 1805, dispersion 3σ or the variation "$\Delta_n$" in the volume of the sample is calculated. In step 1806, it is judged using formula (5) or (11) whether the calculated 3σ decreases below the required value or whether the value of "$\Delta_n$" exceeds the X value that was entered in step 1501.

$$3\sigma < X \quad (11)$$

Figure 12B:
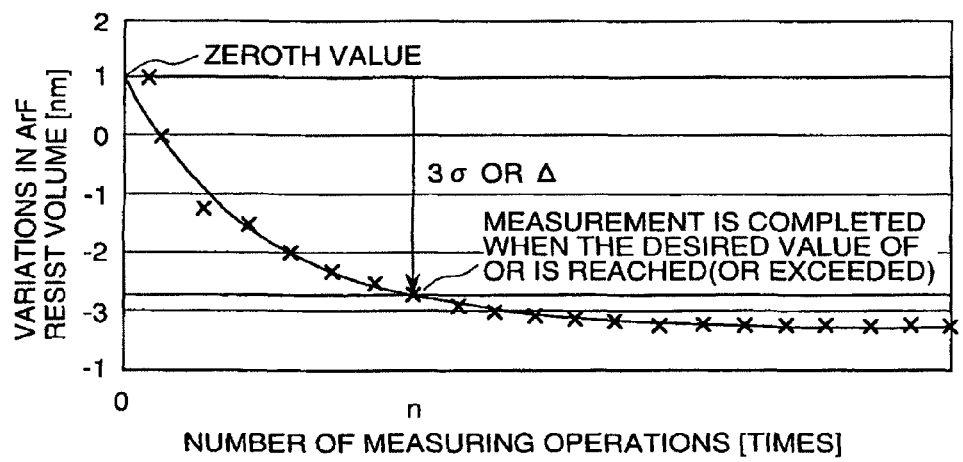

As shown in FIG. 12(b), when the absolute value of the calculated 3σ or "Δ" exceeds the entered X value, the length measuring process will be completed, and in step 1808, the calculated zeroth value $M_{0, n}$, 3σ or "$\Delta_n$" value, and a graph that shows changes in these values are displayed on display unit 26. If X is not exceeded, the length measuring process will be terminated in step 1807 and the finally obtained "N" number of zeroth values $M_{0, N}$, 3σ or "$\Delta_N$," value, and a graph that shows changes in these parameters are displayed.

A sufficient number of scans for achieving the required measuring accuracy can be set by configuring the apparatus in such a manner that as set forth above, the length measuring process will be stopped when the required variation is detected or when the dispersion of zeroth data decreases below the required value. Since the amount of shrinkage greatly depends on the type of photoresist, it is difficult to find the number of measuring operations that is required for the achievement of the required measuring accuracy. According to the present embodiment, however, data setting for achieving the required zeroth data detection accuracy can be easily implemented, irrespective of the type of photoresist. Also, throughput improves since the appropriate number of measuring operations can be set.

Although, in the embodiment of FIG. 18, management based on the number of measuring operations (the number of scans) occurs, this does not limit the embodiment; it is also possible to provide control so that electron beam scanning is interrupted after the amount of shrinkage has been chronologically managed on a unit time basis and the required time of electron beam scanning has been executed.

Figure 19:
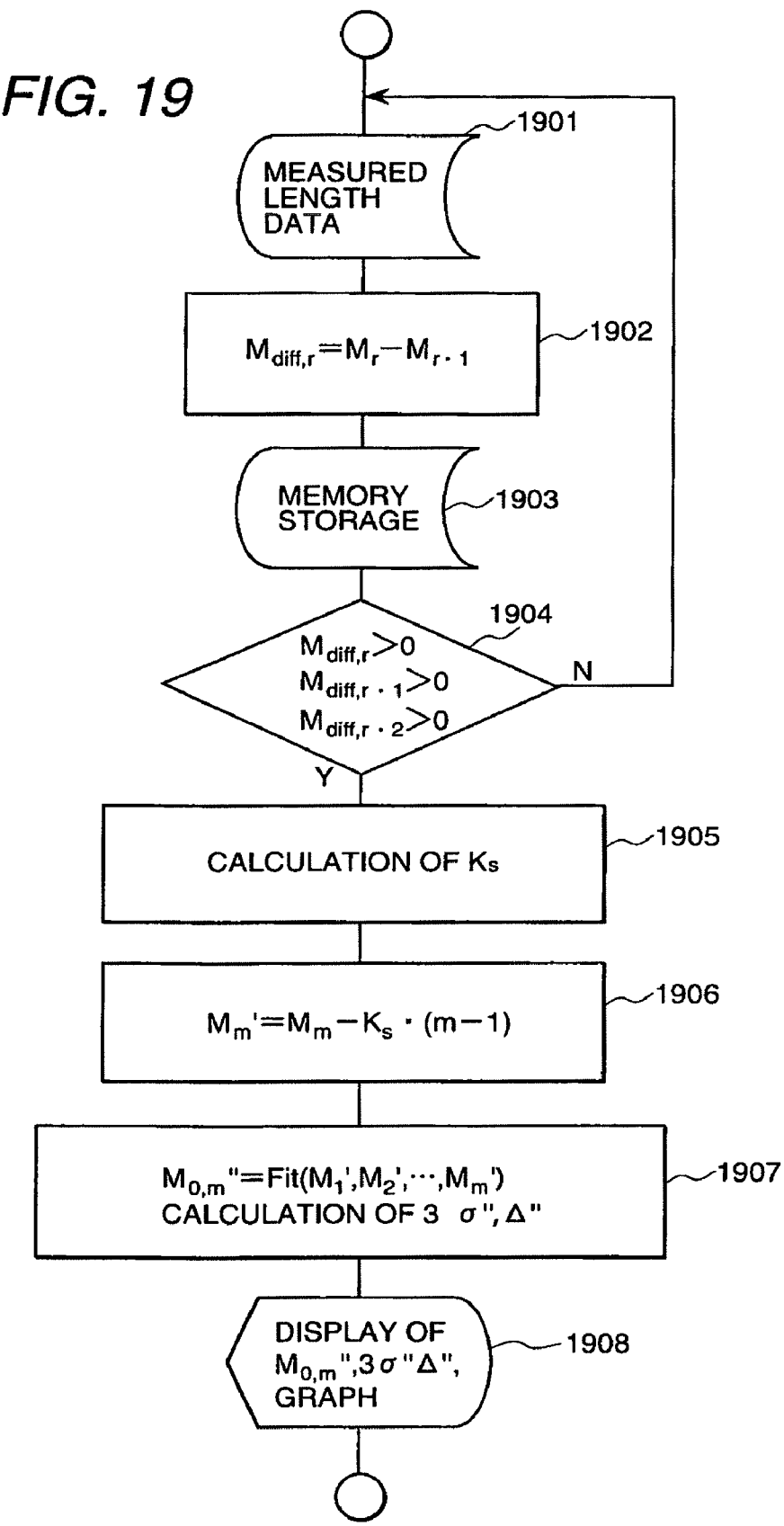
FIG. 19 is a flowchart showing the preferred step in which, irrespective of pattern contamination, the approximate function that denotes shrinkage is to be accurately measured.

FIG. 19 is a flowchart showing the preferred steps for accurately measuring the approximation functions which denote shrinkage, irrespective of contamination sticking to the pattern. In step 1901, length measurements are continuously perormed at one measuring point and measured length data is calculated and stored. In step 1902, the average ("ave, r") of all data from the (r−5)th measured value to the rth measured value is calculated and stored and the difference "$M_{diff, r}$" from the average of all data from the (r−6)th measured value to the (r−1)th measured value is calculated and stored. In step 1904, after the difference "$M_{diff, r}$" has become plus a plurality times in succession, shrinkage stops, then the measured length data is judged to have begun linearly increasing, and the length measuring process is terminated, as shown in FIG. 11(a). After this, in step 1905, the gradient $K_s$ of the linear component is calculated using formula (6). Since the linear component represents the contamination sticking to the surface of the sample, the quantity of contamination which has stuck can be calculated using formula (8).

Even during the shrinkage of the sample, contamination sticks according to the particular number of measuring operations. For this reason, in step 1906, the value obtained by subtracting the linear component from measured length value $M_m$ is calculated as the measured length value $M_m'$ which allows for the quantity of sticking contamination, by applying formula (8) to all the measured length values that were stored into the memory unit. In step 1907, all approximation functions from $M_1'$ to $M_m'$ are newly calculated and then the zeroth values $M_{0, n}''$ obtained by providing linear component correction using formula (9) are calculated and stored. In addition, the calculation of the variation $\Delta''$ in the volume of the sample existing after linear component correction using formula (10) has been provided, and the calculation of the dispersion $3\sigma''$ between zeroth values $M_{0, n}''$ obtained by providing linear component correction are performed and then in step 1908, the zeroth values $M_{0, n}''$ obtained by providing linear component correction, the dispersion $3\sigma''$, the variation $\Delta''$ in the volume of the sample, the newly calculated approximation functions, and other data are displayed on display unit 26. Even if contamination sticks, accurate approximation functions can be obtained by adopting the composition described above.

As set forth above, according to the present embodiment of the invention, during the measurement of such a photoresist, which uses an argon fluoride (ArF) eximer laser as its light source, that changes in shape by the action of the electron beams irradiated for the observation of the sample, the length of the pattern existing before a change in shape occurs can be measured in at least one measuring operation and highly accurate dimension measurement is possible. Automatic length measurement is also possible and dispersion in measured data can be reduced. In this context, there are advantages associated with process management of semiconductor manufacture.

In addition, automatic measurement of variations in the volume of the sample with respect to the quantity of electron beam irradiation becomes possible and a graph of changes can be displayed on the screen. These, in turn, facilitate the examination of the optimal electron beam irradiation conditions for ArF photoresist measurement, and offers an advantage associated with the management of the pattern width during the use of an electron beam apparatus such as a length measuring electron microscope.

Furthermore, it becomes possible to obtain the measured length data existing before the shape of the sample changes, even when sticking impurities are present on the surface of the sample, and to conduct highly accurate dimension measurements.

What is claimed is:

1. A sample dimension measuring method in which the dimensions of the pattern formed on a sample are measured by scanning said sample with electron beams and detecting the electrons released from the scanned section, wherein the dimension measuring method is characterized in that the functions that denote such changes in the rate of decrease of said pattern dimension that occur when electron beams are irradiated to the sample are calculated beforehand and in that the dimensions of the pattern existing before it dimensionally decreases are estimated from said functions and the length data obtained by scanning the surface of the sample.

2. A scanning electron microscope comprising:
an electron source,
a deflector for scanning with the electron beams which are emitted from said electron source,
a detector for detecting the electrons released from a sample by said electron beam scans, and
a control processor for measuring the dimensions of the pattern on said sample in accordance with the output of said detector,
wherein said control processor has a memory unit into which the functions that denote such changes in the rate of decrease of said pattern dimension that occur when electron beams are irradiated to said sample can be stored, and wherein the dimensions of the pattern existing before it dimensionally decreases are calculated from the stored functions mentioned above and the length data obtained by scanning the surface of the sample.

3. The scanning electron microscope as set forth in claim 2 above, wherein more than one function denoting such changes in the rate of decrease of said pattern dimension is stored within said memory unit.

4. The scanning electron microscope as set forth in claim 3 above, wherein said functions are stored inside said memory unit for each optical parameter of the scanning electron microscope.

* * * * *